(12) United States Patent
Mehmet

(10) Patent No.: US 10,296,724 B2
(45) Date of Patent: May 21, 2019

(54) METHOD FOR PREPARING A CUSTOMIZED EXERCISE STRATEGY

(71) Applicant: Tansu Mehmet, Pristina Kosova (RS)

(72) Inventor: Tansu Mehmet, Pristina Kosova (RS)

( * ) Notice: Subject to any disclaimer, the term of this patent is extended or adjusted under 35 U.S.C. 154(b) by 317 days.

(21) Appl. No.: 15/032,741

(22) PCT Filed: Oct. 20, 2014

(86) PCT No.: PCT/TR2014/000386
§ 371 (c)(1),
(2) Date: Apr. 28, 2016

(87) PCT Pub. No.: WO2015/065298
PCT Pub. Date: May 7, 2015

(65) Prior Publication Data
US 2016/0283695 A1 Sep. 29, 2016

(30) Foreign Application Priority Data
Oct. 30, 2013 (TR) .............................. a 2013 12557

(51) Int. Cl.
*G06F 19/00* (2018.01)
*G06Q 50/22* (2018.01)

(52) U.S. Cl.
CPC ......... *G06F 19/3481* (2013.01); *G06Q 50/22* (2013.01)

(58) Field of Classification Search
None
See application file for complete search history.

(56) References Cited

U.S. PATENT DOCUMENTS 5,692,501 A * 12/1997 Minturn .................. A61B 5/00
  600/301
8,690,578 B1 * 4/2014 Nusbaum ............... G09B 19/00
  434/127
9,665,873 B2 * 5/2017 Ackland ............ A63B 24/0075
(Continued)

FOREIGN PATENT DOCUMENTS

WO 2010041001 A1 4/2010
WO 2011045726 A1 4/2011

OTHER PUBLICATIONS

International Search Report for corresponding International Application No. PCT/TR2014/000386.

*Primary Examiner* — Michael Tomaszewski
*Assistant Examiner* — Jay M. Patel
(74) *Attorney, Agent, or Firm* — Egbert Law Offices, PLLC

(57) ABSTRACT

A method in the field of health related fitness is disclosed for preparing and monitoring a customized exercise prescription based on scientific and concrete data and by activating all of the fitness components, and includes the process steps of dividing the strength component value into three separate sub components as lower extremity strength, upper extremity strength and trunk strength, creating an image of fitness map on the display (screen) which shows the ratios of fitness component values according to the age- and gender-related norms, determining exercise strategy by putting the fitness components of a person in order with respect to their priority of effect to health in accordance with the measurements of fitness components of a person, and preparing an exercise prescription which will provide simultaneous improvement of fitness components of a person.

10 Claims, 13 Drawing Sheets

(56) References Cited

U.S. PATENT DOCUMENTS

| | | | | |
|---|---|---|---|---|
| 2003/0027688 | A1* | 2/2003 | Gordon | A63B 24/00 |
| | | | | 482/9 |
| 2004/0220017 | A1 | 11/2004 | Gordon | |
| 2005/0240434 | A1* | 10/2005 | Wooten | G06F 19/3475 |
| | | | | 705/2 |
| 2005/0240444 | A1* | 10/2005 | Wooten | G06F 19/3481 |
| | | | | 705/3 |
| 2007/0197274 | A1* | 8/2007 | Dugan | A63F 13/52 |
| | | | | 463/7 |
| 2008/0046284 | A1* | 2/2008 | Fisher | G06Q 50/22 |
| | | | | 705/2 |
| 2008/0161655 | A1* | 7/2008 | Teller | A61B 5/01 |
| | | | | 600/300 |
| 2010/0022364 | A1* | 1/2010 | Bocchicchio | A63B 21/068 |
| | | | | 482/96 |
| 2011/0281249 | A1* | 11/2011 | Gammell | G16H 10/20 |
| | | | | 434/247 |
| 2012/0040799 | A1* | 2/2012 | Jaquish | A63B 21/00047 |
| | | | | 482/9 |
| 2012/0071733 | A1* | 3/2012 | Grey | G06F 19/3481 |
| | | | | 600/301 |
| 2012/0165703 | A1* | 6/2012 | Bottum | G06F 19/3481 |
| | | | | 600/595 |
| 2013/0053990 | A1* | 2/2013 | Ackland | G06Q 30/02 |
| | | | | 700/91 |
| 2014/0089836 | A1* | 3/2014 | Damani | G06F 19/3418 |
| | | | | 715/771 |

* cited by examiner

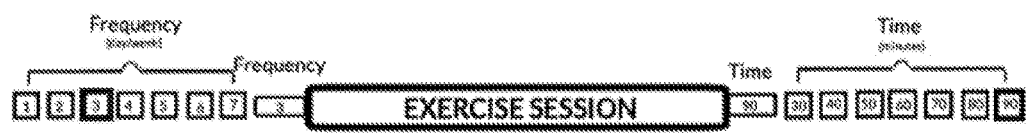
FIG. 10
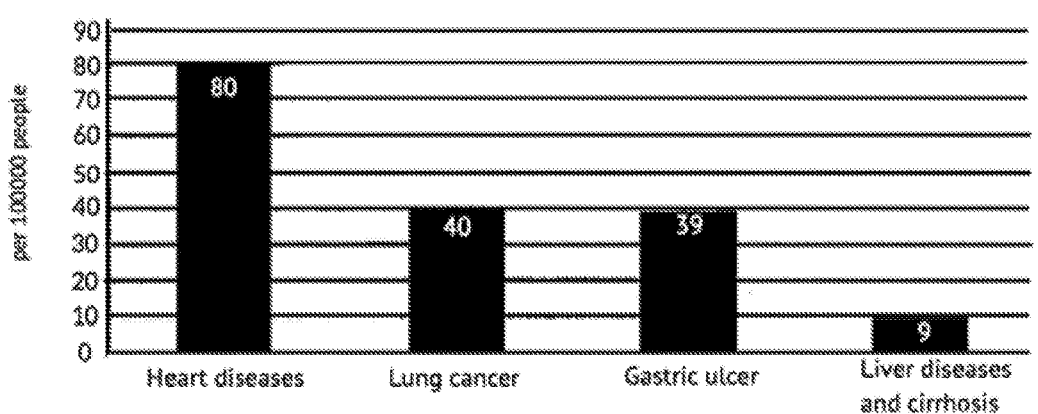
FIG. 11: Table 1

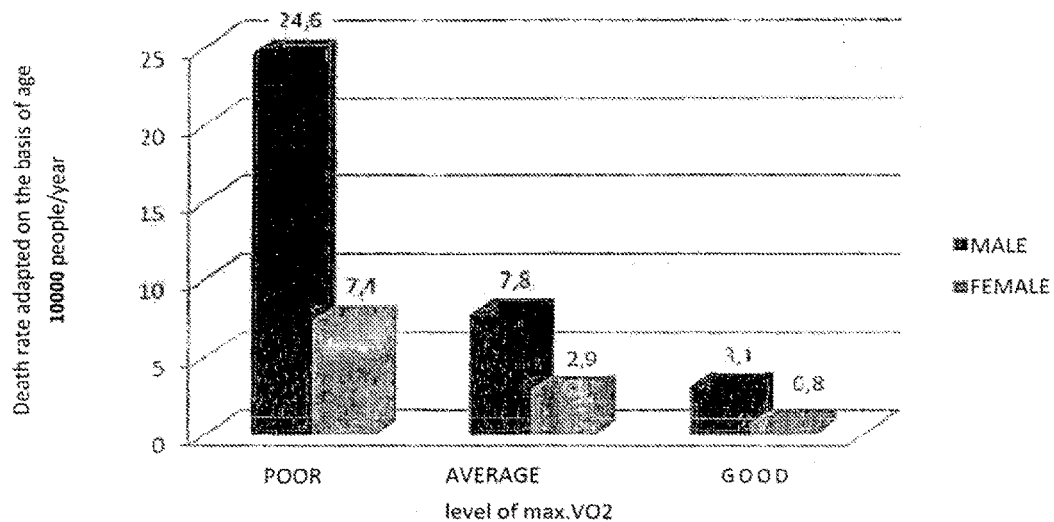
FIG. 12: Table 2
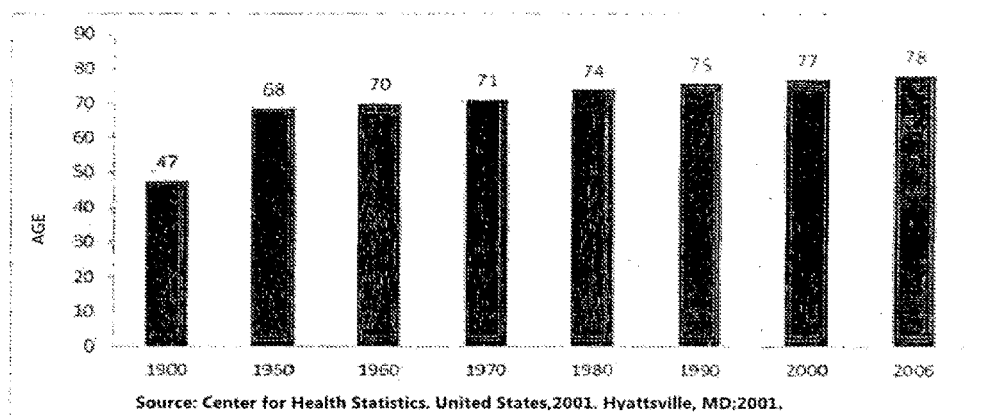
Table 3: Average lifespan of human being according to years
FIG. 13

Source: Department of Health and Human Services, Washinton DC:January 2000.
Table 4: Average lifespan of human being lived healthy and unhealthy Table 12: DIAGRAM OF RULES TO DETERMINE EXERCISE STRATEGY

| Tables of Cardio Strategy Frequencies and Times ||||||||||||||||
|---|---|---|---|---|---|---|---|---|---|---|---|---|---|---|---|
| Frequency | Total Time | Strategy Code | Session Order | Primary Cardio (minutes) | Session Order | Cardio (minutes) | Session Order | Primary Strenght (minutes) | Session Order | Secondary Strenght (minutes) | Session Order | Primary Flexibility (minutes) | Session Order | Secondary Flexibility (minutes) | Total Time | Strategy Frequency |
| 1 | 30 | 1.ST | 1 | 25 | | | | | | | | | 2 | 5 | 30 | 1 |
| 2 | 30 | 1.ST | 1 | 25 | | | | | | | | | 2 | 5 | 30 | 2 |
| 3 | 30 | 1.ST | 1 | 25 | | | | | | | | | 2 | 5 | 30 | 3 |
| 4 | 30 | 1.ST | 1 | 25 | | | | | | | | | 2 | 5 | 30 | 3 |
| 4 | 30 | 2.ST - a | | | | | 1 | 30 | | | | | | | 30 | 1 |
| 5 | 30 | 1.ST | 1 | 25 | | | | | | | | | 2 | 5 | 30 | 3 |
| 5 | 30 | 2.ST - a | | | | | 1 | 30 | | | | | | | 30 | 2 |
| 6 | 30 | 1.ST | 1 | 25 | | | | | | | | | 2 | 5 | 30 | 3 |
| 6 | 30 | 2.ST - a | | | | | 1 | 30 | | | | | | | 30 | 2 |
| 6 | 30 | 3.ST | | | | | | | | | 1 | 30 | | | 30 | 1 |
| 7 | 30 | 1.ST | 1 | 25 | | | | | | | | | 2 | 5 | 30 | 3 |
| 7 | 30 | 2.ST - a | | | | | 1 | 30 | | | | | | | 30 | 2 |
| 7 | 30 | 3.ST | | | | | | | | | 1 | 30 | | | 30 | 2 |
| 1 | 40 | 1.ST | 1 | 35 | | | | | | | | | 2 | 5 | 40 | 1 |
| 2 | 40 | 1.ST | 1 | 35 | | | | | | | | | 2 | 5 | 40 | 2 |
| 3 | 40 | 1.ST | 1 | 35 | | | | | | | | | 2 | 5 | 40 | 3 |
| 4 | 40 | 1.ST | 1 | 35 | | | | | | | | | 2 | 5 | 40 | 3 |
| 4 | 40 | 2.ST - a | | | | | 1 | 40 | | | | | | | 40 | 1 |
| 5 | 40 | 1.ST | 1 | 35 | | | | | | | | | 2 | 5 | 40 | 3 |
| 5 | 40 | 2.ST - a | | | | | 1 | 40 | | | | | | | 40 | 2 |
| 6 | 40 | 1.ST | 1 | 35 | | | | | | | | | 2 | 5 | 40 | 3 |
| 6 | 40 | 2.ST - a | | | | | 1 | 40 | | | | | | | 40 | 2 |
| 6 | 40 | 3.ST | | | | | | | | | 1 | 40 | | | 40 | 1 |
| 7 | 40 | 1.ST | 1 | 35 | | | | | | | | | 2 | 5 | 40 | 3 |
| 7 | 40 | 2.ST - a | | | | | 1 | 40 | | | | | | | 40 | 2 |
| 7 | 40 | 3.ST | | | | | | | | | 1 | 40 | | | 40 | 2 |
| 1 | 50 | 1.ST | 1 | 35 | | | | | 3 | 10 | | | 2 | 5 | 50 | 1 |
| 2 | 50 | 1.ST | 1 | 35 | | | | | 3 | 10 | | | 2 | 5 | 50 | 2 |
| 3 | 50 | 1.ST | 1 | 35 | | | | | 3 | 10 | | | 2 | 5 | 50 | 3 |
| 4 | 50 | 1.ST | 1 | 35 | | | | | 3 | 10 | | | 2 | 5 | 50 | 3 |
| 4 | 50 | 2.ST - a | | | | | 1 | 50 | | | | | | | 50 | 1 |
| 5 | 50 | 1.ST | 1 | 35 | | | | | 3 | 10 | | | 2 | 5 | 50 | 3 |
| 5 | 50 | 2.ST - a | | | | | 1 | 50 | | | | | | | 50 | 2 |
| 6 | 50 | 1.ST | 1 | 35 | | | | | 3 | 10 | | | 2 | 5 | 50 | 3 |
| 6 | 50 | 2.ST - a | | | | | 1 | 50 | | | | | | | 50 | 2 |
| 6 | 50 | 3.ST | | | | | | | | | | 50 | 1 | | 50 | 1 |
| 7 | 50 | 1.ST | 1 | 35 | | | | | 3 | 10 | | | 2 | 5 | 50 | 3 |
| 7 | 50 | 2.ST - a | | | | | 1 | 50 | | | | | | | 50 | 2 |
| 7 | 50 | 3.ST | | | | | | | | | | 50 | 1 | | 50 | 2 |

Table 13a: Rules for preparing exercise session depending on frequency and time in cardio strategy (1.ST.)

FIG. 16

Tables of Cardio Strategy Frequencies and Times

| Frequency | Total Time | Strategy Code | Session Order | Primary Cardio (minutes) | Session Order | Cardio (minutes) | Session Order | Primary Strenght (minutes) | Session Order | Secondary Strenght (minutes) | Session Order | Flexibility (minutes) | Session Order | Secondary Flexibility (minutes) | Total Time | Strategy Frequency |
|---|---|---|---|---|---|---|---|---|---|---|---|---|---|---|---|---|
| 1 | 60 | 1.ST | 1 | 35 | | | | | 3 | 20 | | | 2 | 5 | 60 | 1 |
| 2 | 60 | 1.ST | 1 | 35 | | | | | 3 | 20 | | | 2 | 5 | 60 | 2 |
| 3 | 60 | 1.ST | 1 | 35 | | | | | 3 | 20 | | | 2 | 5 | 60 | 3 |
| 4 | 60 | 1.ST | 1 | 35 | | | | | 3 | 20 | | | 2 | 5 | 60 | 3 |
| 4 | 60 | 2.ST - a | | | 2 | 20 | 1 | 35 | | | | | 3 | 5 | 60 | 1 |
| 5 | 60 | 1.ST | 1 | 35 | | | | | 3 | 20 | | | 2 | 5 | 60 | 3 |
| 5 | 60 | 2.ST - a | | | 2 | 20 | 1 | 35 | | | | | 3 | 5 | 60 | 2 |
| 6 | 60 | 1.ST | 1 | 35 | | | | | 3 | 20 | | | 2 | 5 | 60 | 3 |
| 6 | 60 | 2.ST - a | | | 2 | 20 | 1 | 35 | | | | | 3 | 5 | 60 | 2 |
| 6 | 60 | 3.ST | 1 | 20 | | | | | | | 2 | 40 | | | 60 | 1 |
| 7 | 60 | 1.ST | 1 | 35 | | | | | 3 | 20 | | | 2 | 5 | 60 | 3 |
| 7 | 60 | 2.ST - a | | | 2 | 20 | 1 | 35 | | | | | 3 | 5 | 60 | 2 |
| 7 | 60 | 3.ST | 1 | 20 | | | | | | | 2 | 40 | | | 60 | 2 |
| 1 | 70 | 1.ST | 1 | 35 | | | | | 3 | 25 | 3 | | 2 | 10 | 70 | 1 |
| 2 | 70 | 1.ST | 1 | 35 | | | | | 3 | 25 | 3 | | 2 | 10 | 70 | 2 |
| 3 | 70 | 1.ST | 1 | 35 | | | | | 3 | 25 | 3 | | 2 | 10 | 70 | 3 |
| 4 | 70 | 1.ST | 1 | 35 | | | | | 3 | 25 | 3 | | 2 | 10 | 70 | 3 |
| 4 | 70 | 2.ST - a | | | 2 | 20 | 1 | 45 | | | | | 3 | 5 | 70 | 1 |
| 5 | 70 | 1.ST | 1 | 35 | | | | | 3 | 25 | | | 2 | 10 | 70 | 3 |
| 5 | 70 | 2.ST - a | | | 2 | 20 | 1 | 45 | | | | | 3 | 5 | 70 | 2 |
| 6 | 70 | 1.ST | 1 | 35 | | | | | 3 | 25 | | | 2 | 10 | 70 | 3 |
| 6 | 70 | 2.ST - a | | | 2 | 20 | 1 | 45 | | | | | 3 | 5 | 70 | 2 |
| 6 | 70 | 3.ST | 1 | 20 | | | | | | | 2 | 50 | | | 70 | 1 |
| 7 | 70 | 1.ST | 1 | 35 | | | | | 3 | 25 | | | 2 | 10 | 70 | 3 |
| 7 | 70 | 2.ST - a | | | 2 | 20 | 1 | 45 | | | | | 3 | 5 | 70 | 2 |
| 7 | 70 | 3.ST | 1 | 20 | | | | | | | 2 | 50 | | | 70 | 2 |
| 1 | 80 | 1.ST | 1 | 35 | | | | | 2 | 25 | 3 | 20 | | | 80 | 1 |
| 2 | 80 | 1.ST | 1 | 35 | | | | | 2 | 25 | 3 | 20 | | | 80 | 2 |
| 3 | 80 | 1.ST | 1 | 35 | | | | | 2 | 25 | 3 | 20 | | | 80 | 3 |
| 4 | 80 | 1.ST | 1 | 35 | | | | | 2 | 25 | 3 | 20 | | | 80 | 3 |
| 4 | 80 | 2.ST - a | | | 2 | 30 | 1 | 45 | | | | | 3 | 5 | 80 | 1 |
| 5 | 80 | 1.ST | 1 | 35 | | | | | 2 | 25 | 3 | 20 | | | 80 | 3 |
| 5 | 80 | 2.ST - a | | | 2 | 30 | 1 | 45 | | | | | 3 | 5 | 80 | 2 |
| 6 | 80 | 1.ST | 1 | 35 | | | | | 2 | 25 | 3 | 20 | | | 80 | 3 |
| 6 | 80 | 2.ST - a | | | 2 | 30 | 1 | 45 | | | | | 3 | 5 | 80 | 2 |
| 6 | 80 | 3.ST | 1 | 20 | | | | | | | 2 | 60 | | | 80 | 1 |
| 7 | 80 | 1.ST | 1 | 35 | | | | | 2 | 25 | 3 | 20 | | | 80 | 3 |
| 7 | 80 | 2.ST - a | | | 2 | 30 | 1 | 45 | | | | | 3 | 5 | 80 | 2 |
| 7 | 80 | 3.ST | 1 | 20 | | | | | | | 2 | 60 | | | 80 | 2 |
| 1 | 90 | 1.ST | 1 | 40 | | | | | 2 | 30 | 3 | 20 | | | 90 | 1 |
| 2 | 90 | 1.ST | 1 | 40 | | | | | 2 | 30 | 3 | 20 | | | 90 | 2 |
| 3 | 90 | 1.ST | 1 | 40 | | | | | 2 | 30 | 3 | 20 | | | 90 | 3 |
| 4 | 90 | 1.ST | 1 | 40 | | | | | 2 | 30 | 3 | 20 | | | 90 | 3 |
| 4 | 90 | 2.ST - a | | | 2 | 30 | 1 | 45 | | | 3 | 15 | | | 90 | 1 |
| 5 | 90 | 1.ST | 1 | 40 | | | | | 2 | 30 | 3 | 20 | | | 90 | 3 |
| 5 | 90 | 2.ST - a | | | 2 | 30 | 1 | 45 | | | 3 | 15 | | | 90 | 2 |
| 6 | 90 | 1.ST | 1 | 40 | | | | | 2 | 30 | 3 | 20 | | | 90 | 3 |
| 6 | 90 | 2.ST - a | | | 2 | 30 | 1 | 45 | | | 3 | 15 | | | 90 | 2 |
| 6 | 90 | 3.ST | 1 | 30 | | | | | | | 2 | 60 | | | 90 | 1 |
| 7 | 90 | 1.ST | 1 | 40 | | | | | 2 | 30 | 3 | 20 | | | 90 | 3 |
| 7 | 90 | 2.ST - a | | | 2 | 30 | 1 | 45 | | | 3 | 15 | | | 90 | 2 |
| 7 | 90 | 3.ST | 1 | 30 | | | | | | | 2 | 60 | | | 90 | 2 |

Table 13b: Rules for preparing exercise session depending on frequency and time in cardio strategy (1.ST.) - continued

FIG. 17

| Table of Strenght Strategy Frequencies and Times |||||||||||||||||
|---|---|---|---|---|---|---|---|---|---|---|---|---|---|---|---|---|
| Frequency | Total Time | Strategy Code | Primary Strenght | Session Order | 1.ST Priority Area | Session Order | 2.st Priority Area | Session Order | 3.st Priority Area | Session Order | Primary Cardio | Session Order | Secondary Cardio | Session Order | Primary Flexibility | Session Order | Secondary Flexibility | Total Time | Strategy Frequency |
| | | | minutes | | Set to be Done | | Set to be Done | | Set to be Done | | | | | | | | | | |
| 1 | 30 | 2.ST - a | 30 | 1 | 4 | 2 | 4 | 3 | 4 | | | | | | | | | 30 | 1 |
| 2 | 30 | 2.ST - a | 30 | 1 | 4 | 2 | 4 | 3 | 4 | | | | | | | | | 30 | 2 |
| 3 | 30 | 2.ST - a | 30 | 1 | 4 | 2 | 4 | 3 | 4 | | | | | | | | | 30 | 2 |
| 3 | 30 | 1.ST | | | | | | | | 1 | 25 | | | | | 2 | 5 | 30 | 1 |
| 4 | 30 | 2.ST - a | 30 | 1 | 4 | 2 | 4 | 3 | 4 | | | | | | | | | 30 | 2 |
| 4 | 30 | 2.ST - b | 30 | 2 | 4 | 1 | 4 | 3 | 4 | | | | | | | | | 30 | 1 |
| 4 | 30 | 1.ST | 30 | | | | | | | 1 | 25 | | | | | 2 | 5 | 30 | 1 |
| 5 | 30 | 2.ST - a | 30 | 1 | 4 | 2 | 4 | 3 | 4 | | | | | | | | | 30 | 1 |
| 5 | 30 | 2.ST - b | 30 | 2 | 4 | 1 | 4 | 3 | 4 | | | | | | | | | 30 | 1 |
| 5 | 30 | 2.ST - c | 30 | 3 | 4 | 1 | 4 | 2 | 4 | | | | | | | | | 30 | 1 |
| 5 | 30 | 1.ST | | | | | | | | 1 | 25 | | | | | 2 | 5 | 30 | 2 |
| 6 | 30 | 2.ST - a | 30 | 1 | 4 | 2 | 4 | 3 | 4 | | | | | | | | | 30 | 2 |
| 6 | 30 | 2.ST - b | 30 | 2 | 4 | 1 | 4 | 3 | 4 | | | | | | | | | 30 | 1 |
| 6 | 30 | 2.ST - c | 30 | 3 | 4 | 1 | 4 | 2 | 4 | | | | | | | | | 30 | 1 |
| 6 | 30 | 1.ST | | | | | | | | 1 | 25 | | | | | 2 | 5 | 30 | 2 |
| 7 | 30 | 2.ST - a | 30 | 1 | 4 | 2 | 4 | 3 | 4 | | | | | | | | | 30 | 2 |
| 7 | 30 | 2.ST - b | 30 | 2 | 4 | 1 | 4 | 3 | 4 | | | | | | | | | 30 | 1 |
| 7 | 30 | 2.ST - c | 30 | 3 | 4 | 1 | 4 | 2 | 4 | | | | | | | | | 30 | 1 |
| 7 | 30 | 1.ST | | | | | | | | 1 | 25 | | | | | 2 | 5 | 30 | 2 |
| 7 | 30 | 3.ST | | | | | | | | | | | | 1 | 30 | | | 30 | 1 |
| 1 | 40 | 2.ST - a | 40 | 1 | 6 | 2 | 6 | 3 | 6 | | | | | | | | | 40 | 1 |
| 2 | 40 | 2.ST - a | 40 | 1 | 6 | 2 | 6 | 3 | 6 | | | | | | | | | 40 | 2 |
| 3 | 40 | 2.ST - a | 40 | 1 | 6 | 2 | 6 | 3 | 6 | | | | | | | | | 40 | 2 |
| 3 | 40 | 1.ST | | | | | | | | 1 | 35 | | | | | 2 | 5 | 40 | 1 |
| 4 | 40 | 2.ST - a | 40 | 1 | 6 | 2 | 6 | 3 | 6 | | | | | | | | | 40 | 2 |
| 4 | 40 | 2.ST - b | 40 | 2 | 6 | 1 | 6 | 3 | 6 | | | | | | | | | 40 | 1 |
| 4 | 40 | 1.ST | 40 | | | | | | | 1 | 35 | | | | | 2 | 5 | 40 | 1 |
| 5 | 40 | 2.ST - a | 40 | 1 | 6 | 2 | 6 | 3 | 6 | | | | | | | | | 40 | 1 |
| 5 | 40 | 2.ST - b | 40 | 2 | 6 | 1 | 6 | 3 | 6 | | | | | | | | | 40 | 1 |
| 5 | 40 | 2.ST - c | 40 | 3 | 6 | 1 | 6 | 2 | 6 | | | | | | | | | 40 | 1 |
| 5 | 40 | 1.ST | | | | | | | | 1 | 35 | | | | | 2 | 5 | 40 | 2 |
| 6 | 40 | 2.ST - a | 40 | 1 | 6 | 2 | 6 | 3 | 6 | | | | | | | | | 40 | 2 |
| 6 | 40 | 2.ST - b | 40 | 2 | 6 | 1 | 6 | 3 | 6 | | | | | | | | | 40 | 1 |
| 6 | 40 | 2.ST - c | 40 | 3 | 6 | 1 | 6 | 2 | 6 | | | | | | | | | 40 | 1 |
| 6 | 40 | 1.ST | | | | | | | | 1 | 35 | | | | | 2 | 5 | 40 | 2 |
| 7 | 40 | 2.ST - a | 40 | 1 | 6 | 2 | 6 | 3 | 6 | | | | | | | | | 40 | 2 |
| 7 | 40 | 2.ST - b | 40 | 2 | 6 | 1 | 6 | 3 | 6 | | | | | | | | | 40 | 1 |
| 7 | 40 | 2.ST - c | 40 | 3 | 6 | 1 | 6 | 2 | 6 | | | | | | | | | 40 | 1 |
| 7 | 40 | 1.ST | | | | | | | | 1 | 35 | | | | | 2 | 5 | 40 | 2 |
| 7 | 40 | 3.ST | | | | | | | | | | | | 1 | 40 | | | 40 | 1 |
| 1 | 50 | 2.ST - a | 50 | 1 | 7 | 2 | 7 | 3 | 7 | | | | | | | | | 50 | 1 |
| 2 | 50 | 2.ST - a | 50 | 1 | 7 | 2 | 7 | 3 | 7 | | | | | | | | | 50 | 2 |
| 3 | 50 | 2.ST - a | 50 | 1 | 7 | 2 | 7 | 3 | 7 | | | | | | | | | 50 | 2 |
| 3 | 50 | 1.ST | | | | | | | | 1 | 40 | | | | | 2 | 10 | 50 | 1 |
| 4 | 50 | 2.ST - a | 50 | 1 | 7 | 2 | 7 | 3 | 7 | | | | | | | | | 50 | 2 |
| 4 | 50 | 2.ST - b | 50 | 2 | 7 | 1 | 7 | 3 | 7 | | | | | | | | | 50 | 1 |
| 4 | 50 | 1.ST | 50 | | | | | | | 1 | 40 | | | | | 2 | 10 | 100 | 1 |
| 5 | 50 | 2.ST - a | 50 | 1 | 7 | 2 | 7 | 3 | 7 | | | | | | | | | 50 | 1 |
| 5 | 50 | 2.ST - b | 50 | 2 | 7 | 1 | 7 | 3 | 7 | | | | | | | | | 50 | 1 |
| 5 | 50 | 2.ST - c | 50 | 3 | 7 | 1 | 7 | 2 | 7 | | | | | | | | | 50 | 1 |
| 5 | 50 | 1.ST | | | | | | | | 1 | 40 | | | | | 2 | 10 | 50 | 2 |
| 6 | 50 | 2.ST - a | 50 | 1 | 7 | 2 | 7 | 3 | 7 | | | | | | | | | 50 | 2 |
| 6 | 50 | 2.ST - b | 50 | 2 | 7 | 1 | 7 | 3 | 7 | | | | | | | | | 50 | 1 |
| 6 | 50 | 2.ST - c | 50 | 3 | 7 | 1 | 7 | 2 | 7 | | | | | | | | | 50 | 1 |
| 6 | 50 | 1.ST | | | | | | | | 1 | 40 | | | | | 2 | 10 | 50 | 2 |
| 7 | 50 | 2.ST - a | 50 | 1 | 7 | 2 | 7 | 3 | 7 | | | | | | | | | 50 | 2 |
| 7 | 50 | 2.ST - b | 50 | 2 | 7 | 1 | 7 | 3 | 7 | | | | | | | | | 50 | 1 |
| 7 | 50 | 2.ST - c | 50 | 3 | 7 | 1 | 7 | 2 | 7 | | | | | | | | | 50 | 1 |
| 7 | 50 | 1.ST | | | | | | | | 1 | 40 | | | | | 2 | 10 | 50 | 2 |
| 7 | 50 | 3.ST | | | | | | | | | | | | 1 | 50 | | | 50 | 1 |

Table 14a: Rules for preparing exercise session depending on frequency and time in strenght strategy (2.ST.)

FIG. 18

Table of Strenght Strategy Frequencies and Times

| Frequency | Total Time | Strategy Code | Primary Strenght | Session Order | 1.ST Priority Area | Session Order | 2.st Priority Area | Session Order | 3.st Priority Area | Session Order | Primary Cardio | Session Order | Secondary Cardio | Session Order | Primary Flexibility | Session Order | Secondary Flexibility | Total Time | Strategy Frequency |
|---|---|---|---|---|---|---|---|---|---|---|---|---|---|---|---|---|---|---|---|
| | | | minutes | | Set to be Done | | Set to be Done | | Set to be Done | | | | | | | | | | |
| 1 | 60 | 2.ST - a | 35 | 1 | 5 | 2 | 5 | 3 | 5 | | | 4 | 20 | | | 5 | 5 | 60 | 1 |
| 2 | 60 | 2.ST - a | 35 | 1 | 5 | 2 | 5 | 3 | 5 | | | 4 | 20 | | | 5 | 5 | 60 | 2 |
| 3 | 60 | 2.ST - a | 35 | 1 | 5 | 2 | 5 | 3 | 5 | | | 4 | 20 | | | 5 | 5 | 60 | 3 |
| 4 | 60 | 2.ST - a | 35 | 1 | 5 | 2 | 5 | 3 | 5 | | | 4 | 20 | | | 5 | 5 | 60 | 2 |
| 4 | 60 | 2.ST - b | 35 | 2 | 5 | 1 | 5 | 3 | 5 | | | 4 | 20 | | | 5 | 5 | 60 | 2 |
| 5 | 60 | 2.ST - a | 35 | 1 | 5 | 2 | 5 | 3 | 5 | | | 4 | 20 | | | 5 | 5 | 60 | 2 |
| 5 | 60 | 2.ST - b | 35 | 2 | 5 | 1 | 5 | 3 | 5 | | | 4 | 20 | | | 5 | 5 | 60 | 2 |
| 5 | 60 | 2.ST - c | 35 | 3 | 5 | 1 | 5 | 2 | 5 | | | 4 | 20 | | | 5 | 5 | 60 | 1 |
| 6 | 60 | 2.ST - a | 35 | 1 | 5 | 2 | 5 | 3 | 5 | | | 4 | 20 | | | 5 | 5 | 60 | 2 |
| 6 | 60 | 2.ST - b | 35 | 2 | 5 | 1 | 5 | 3 | 5 | | | 4 | 20 | | | 5 | 5 | 60 | 2 |
| 6 | 60 | 2.ST - c | 35 | 3 | 5 | 1 | 5 | 2 | 5 | | | 4 | 20 | | | 5 | 5 | 60 | 2 |
| 7 | 60 | 2.ST - a | 35 | 1 | 5 | 2 | 5 | 3 | 5 | | | 4 | 20 | | | 5 | 5 | 60 | 2 |
| 7 | 60 | 2.ST - b | 35 | 2 | 5 | 1 | 5 | 3 | 5 | | | 4 | 20 | | | 5 | 5 | 60 | 2 |
| 7 | 60 | 2.ST - c | 35 | 3 | 5 | 1 | 5 | 2 | 5 | | | 4 | 20 | | | 5 | 5 | 60 | 2 |
| 7 | 60 | 3.ST | | | | | | | | | | | | 1 | 60 | | | 60 | 1 |
| 1 | 70 | 2.ST - a | 45 | 1 | 6 | 2 | 6 | 3 | 6 | | | 4 | 20 | | | 5 | 5 | 70 | 1 |
| 2 | 70 | 2.ST - a | 45 | 1 | 6 | 2 | 6 | 3 | 6 | | | 4 | 20 | | | 5 | 5 | 70 | 2 |
| 3 | 70 | 2.ST - a | 45 | 1 | 6 | 2 | 6 | 3 | 6 | | | 4 | 20 | | | 5 | 5 | 70 | 3 |
| 4 | 70 | 2.ST - a | 45 | 1 | 6 | 2 | 6 | 3 | 6 | | | 4 | 20 | | | 5 | 5 | 70 | 2 |
| 4 | 70 | 2.ST - b | 45 | 2 | 6 | 1 | 6 | 3 | 6 | | | 4 | 20 | | | 5 | 5 | 70 | 2 |
| 5 | 70 | 2.ST - a | 45 | 1 | 6 | 2 | 6 | 3 | 6 | | | 4 | 20 | | | 5 | 5 | 70 | 2 |
| 5 | 70 | 2.ST - b | 45 | 2 | 6 | 1 | 6 | 3 | 6 | | | 4 | 20 | | | 5 | 5 | 70 | 2 |
| 5 | 70 | 2.ST - c | 45 | 3 | 6 | 1 | 6 | 2 | 6 | | | 4 | 20 | | | 5 | 5 | 70 | 1 |
| 6 | 70 | 2.ST - a | 45 | 1 | 6 | 2 | 6 | 3 | 6 | | | 4 | 20 | | | 5 | 5 | 70 | 2 |
| 6 | 70 | 2.ST - b | 45 | 2 | 6 | 1 | 6 | 3 | 6 | | | 4 | 20 | | | 5 | 5 | 70 | 2 |
| 6 | 70 | 2.ST - c | 45 | 3 | 6 | 1 | 6 | 2 | 6 | | | 4 | 20 | | | 5 | 5 | 70 | 2 |
| 7 | 70 | 2.ST - a | 45 | 1 | 6 | 2 | 6 | 3 | 6 | | | 4 | 20 | | | 5 | 5 | 70 | 2 |
| 7 | 70 | 2.ST - b | 45 | 2 | 6 | 1 | 6 | 3 | 6 | | | 4 | 20 | | | 5 | 5 | 70 | 2 |
| 7 | 70 | 2.ST - c | 45 | 3 | 6 | 1 | 6 | 2 | 6 | | | 4 | 20 | | | 5 | 5 | 70 | 2 |
| 7 | 70 | 3.ST | 0 | | | | | | | 1 | 20 | 2 | 50 | | | | | 70 | 1 |
| 1 | 80 | 2.ST - a | 45 | 1 | 6 | 2 | 6 | 3 | 6 | | | 4 | 30 | | | 5 | 5 | 80 | 1 |
| 2 | 80 | 2.ST - a | 45 | 1 | 6 | 2 | 6 | 3 | 6 | | | 4 | 30 | | | 5 | 5 | 80 | 2 |
| 3 | 80 | 2.ST - a | 45 | 1 | 6 | 2 | 6 | 3 | 6 | | | 4 | 30 | | | 5 | 5 | 80 | 3 |
| 4 | 80 | 2.ST - a | 45 | 1 | 6 | 2 | 6 | 3 | 6 | | | 4 | 30 | | | 5 | 5 | 80 | 2 |
| 4 | 80 | 2.ST - b | 45 | 2 | 6 | 1 | 6 | 3 | 6 | | | 4 | 30 | | | 5 | 5 | 80 | 2 |
| 5 | 80 | 2.ST - a | 45 | 1 | 6 | 2 | 6 | 3 | 6 | | | 4 | 30 | | | 5 | 5 | 80 | 2 |
| 5 | 80 | 2.ST - b | 45 | 2 | 6 | 1 | 6 | 3 | 6 | | | 4 | 30 | | | 5 | 5 | 80 | 2 |
| 5 | 80 | 2.ST - c | 45 | 3 | 6 | 1 | 6 | 2 | 6 | | | 4 | 30 | | | 5 | 5 | 80 | 1 |
| 6 | 80 | 2.ST - a | 45 | 1 | 6 | 2 | 6 | 3 | 6 | | | 4 | 30 | | | 5 | 5 | 80 | 2 |
| 6 | 80 | 2.ST - b | 45 | 2 | 6 | 1 | 6 | 3 | 6 | | | 4 | 30 | | | 5 | 5 | 80 | 2 |
| 6 | 80 | 2.ST - c | 45 | 3 | 6 | 1 | 6 | 2 | 6 | | | 4 | 30 | | | 5 | 5 | 80 | 2 |
| 7 | 80 | 2.ST - a | 45 | 1 | 6 | 2 | 6 | 3 | 6 | | | 4 | 30 | | | 5 | 5 | 80 | 2 |
| 7 | 80 | 2.ST - b | 45 | 2 | 6 | 1 | 6 | 3 | 6 | | | 4 | 30 | | | 5 | 5 | 80 | 2 |
| 7 | 80 | 2.ST - c | 45 | 3 | 6 | 1 | 6 | 2 | 6 | | | 4 | 30 | | | 5 | 5 | 80 | 2 |
| 7 | 80 | 3.ST | | | | | | | | 1 | 20 | 2 | 60 | | | | | 80 | 1 |
| 1 | 90 | 2.ST - a | 45 | 1 | 6 | 2 | 6 | 3 | 6 | | | 4 | 30 | 5 | 15 | | | 90 | 1 |
| 2 | 90 | 2.ST - a | 45 | 1 | 6 | 2 | 6 | 3 | 6 | | | 4 | 30 | 5 | 15 | | | 90 | 2 |
| 3 | 90 | 2.ST - a | 45 | 1 | 6 | 2 | 6 | 3 | 6 | | | 4 | 30 | 5 | 15 | | | 90 | 3 |
| 4 | 90 | 2.ST - a | 45 | 1 | 6 | 2 | 6 | 3 | 6 | | | 4 | 30 | 5 | 15 | | | 90 | 2 |
| 4 | 90 | 2.ST - b | 45 | 2 | 6 | 1 | 6 | 3 | 6 | | | 4 | 30 | 5 | 15 | | | 90 | 2 |
| 5 | 90 | 2.ST - a | 45 | 1 | 6 | 2 | 6 | 3 | 6 | | | 4 | 30 | 5 | 15 | | | 90 | 2 |
| 5 | 90 | 2.ST - b | 45 | 2 | 6 | 1 | 6 | 3 | 6 | | | 4 | 30 | 5 | 15 | | | 90 | 2 |
| 5 | 90 | 2.ST - c | 45 | 3 | 6 | 1 | 6 | 2 | 6 | | | 4 | 30 | 5 | 15 | | | 90 | 1 |
| 6 | 90 | 2.ST - a | 45 | 1 | 6 | 2 | 6 | 3 | 6 | | | 4 | 30 | 5 | 15 | | | 90 | 2 |
| 6 | 90 | 2.ST - b | 45 | 2 | 6 | 1 | 6 | 3 | 6 | | | 4 | 30 | 5 | 15 | | | 90 | 2 |
| 6 | 90 | 2.ST - c | 45 | 3 | 6 | 1 | 6 | 2 | 6 | | | 4 | 30 | 5 | 15 | | | 90 | 2 |
| 7 | 90 | 2.ST - a | 45 | 1 | 6 | 2 | 6 | 3 | 6 | | | 4 | 30 | 5 | 15 | | | 90 | 2 |
| 7 | 90 | 2.ST - b | 45 | 2 | 6 | 1 | 6 | 3 | 6 | | | 4 | 30 | 5 | 15 | | | 90 | 2 |
| 7 | 90 | 2.ST - c | 45 | 3 | 6 | 1 | 6 | 2 | 6 | | | 4 | 30 | 5 | 15 | | | 90 | 2 |
| 7 | 90 | 3.ST | | | | | | | | 1 | 30 | 2 | 60 | | | | | 90 | 1 |

Table 14b: Rules for preparing exercise session depending on frequency and time in strenght strategy (2.ST) - continued

FIG. 19

| Table of Flexibility Strategy, Frequencies and Times | | | | | | | | | | | | | | | |
|---|---|---|---|---|---|---|---|---|---|---|---|---|---|---|---|
| Frequency | Total Time | Strategy code | Session Order | Primary Cardio (minutes) | Session Order | Secondary Cardio (minutes) | Session Order | Primary Strenght (minutes) | Session Order | Secondary Strenght (minutes) | Session Order | Primary Flexibility (minutes) | Session Order | Secondary Flexibility (minutes) | Total Time | Strategy Frequencie |
| 1 | 30 | 3.ST | | | | | | | | | 1 | 30 | | | 30 | 1 |
| 2 | 30 | 3.ST | | | | | | | | | 1 | 30 | | | 30 | 1 |
| 3 | 30 | 3.ST | | | | | | | | | 1 | 30 | | | 30 | 1 |
| 4 | 30 | 3.ST | | | | | | | | | 1 | 30 | | | 30 | 3 |
| 4 | 30 | 1.ST | 1 | 25 | | | | | | | | | 2 | 5 | 30 | 1 |
| 5 | 30 | 3.ST | | | | | | | | | 1 | 30 | | | 30 | 3 |
| 5 | 30 | 1.ST | 1 | 25 | | | | | | | | | 2 | 5 | 30 | 2 |
| 6 | 30 | 3.ST | | | | | | | | | 1 | 30 | | | 30 | 3 |
| 6 | 30 | 1.ST | 1 | 25 | | | | | | | | | 2 | 5 | 30 | 2 |
| 6 | 30 | 2.ST - a | | | | | 1 | 30 | | | | | | | 30 | 1 |
| 7 | 30 | 3.ST | | | | | | | | | 1 | 30 | | | 30 | 3 |
| 7 | 30 | 1.ST | 1 | 25 | | | | | | | | | 2 | 5 | 30 | 2 |
| 7 | 30 | 2.ST - a | | | | | 1 | 30 | | | | | | | 30 | 2 |
| 1 | 40 | 3.ST | | | | | | | | | 1 | 40 | | | 40 | 1 |
| 2 | 40 | 3.ST | | | | | | | | | 1 | 40 | | | 40 | 1 |
| 3 | 40 | 3.ST | | | | | | | | | 1 | 40 | | | 40 | 1 |
| 4 | 40 | 3.ST | | | | | | | | | 1 | 40 | | | 40 | 3 |
| 4 | 40 | 1.ST | 1 | 35 | | | | | | | | | 2 | 5 | 40 | 1 |
| 5 | 40 | 3.ST | | | | | | | | | 1 | 40 | | | 40 | 3 |
| 5 | 40 | 1.ST | 1 | 35 | | | | | | | | | 2 | 5 | 40 | 2 |
| 6 | 40 | 3.ST | | | | | | | | | 1 | 40 | | | 40 | 3 |
| 6 | 40 | 1.ST | 1 | 35 | | | | | | | | | 2 | 5 | 40 | 2 |
| 6 | 40 | 2.ST - a | | | | | 1 | 40 | | | | | | | 40 | 1 |
| 7 | 40 | 3.ST | | | | | | | | | 1 | 40 | | | 40 | 3 |
| 7 | 40 | 1.ST | 1 | 35 | | | | | | | | | 2 | 5 | 40 | 2 |
| 7 | 40 | 2.ST - a | | | | | 1 | 40 | | | | | | | 40 | 2 |
| 1 | 50 | 3.ST | | | | | | | | | 1 | 50 | | | 50 | 1 |
| 2 | 50 | 3.ST | | | | | | | | | 1 | 50 | | | 50 | 1 |
| 3 | 50 | 3.ST | | | | | | | | | 1 | 50 | | | 50 | 1 |
| 4 | 50 | 3.ST | | | | | | | | | 1 | 50 | | | 50 | 3 |
| 4 | 50 | 1.ST | 1 | 35 | | | | | 3 | 10 | | | 2 | 5 | 50 | 1 |
| 5 | 50 | 3.ST | | | | | | | | | 1 | 50 | | | 50 | 3 |
| 5 | 50 | 1.ST | 1 | 35 | | | | | 3 | 10 | | | 2 | 5 | 50 | 2 |
| 6 | 50 | 3.ST | | | | | | | | | 1 | 50 | | | 50 | 3 |
| 6 | 50 | 1.ST | 1 | 35 | | | | | 3 | 10 | | | 2 | 5 | 50 | 2 |
| 6 | 50 | 2.ST - a | | | | | 1 | 30 | | | 2 | 20 | | | 50 | 1 |
| 7 | 50 | 3.ST | | | | | | | | | 1 | 50 | | | 50 | 3 |
| 7 | 50 | 1.ST | 1 | 35 | | | | | 3 | 10 | | | 2 | 5 | 50 | 2 |
| 7 | 50 | 2.ST - a | | | | | 1 | 30 | | | 2 | 20 | | | 50 | 2 |

Table 15a: Rules for preparing exercise session depending on frequency and time in flexibility strategy (3.ST.)

FIG. 20

| Table of Flexibility Strategy, Frequencies and Times | | | | | | | | | | | | | | | | | |
|---|---|---|---|---|---|---|---|---|---|---|---|---|---|---|---|---|---|
| Frequency | Total time | Strategy code | Session Order | Primary Cardio (minutes) | Session Order | Secondary Cardio (minutes) | Session Order | Primary Strenght (minutes) | Session Order | Secondary Strenght (minutes) | Session Order | Primary Flexibility (minutes) | Session Order | Secondary Flexibility (minutes) | Total Time | Strategy Frequencie |
| 1 | 60 | 3.ST | | | | | | | | | 1 | 60 | | | 60 | 1 |
| 2 | 60 | 3.ST | | | | | | | | | 1 | 60 | | | 60 | 1 |
| 3 | 60 | 3.ST | | | | | | | | | 1 | 60 | | | 60 | 1 |
| 4 | 60 | 3.ST | | | | | | | | | 1 | 60 | | | 60 | 3 |
| 4 | 60 | 1.ST | 1 | 35 | | | | | 3 | 20 | | | 2 | 5 | 60 | 1 |
| 5 | 60 | 3.ST | | | | | | | | | 1 | 60 | | | 60 | 3 |
| 5 | 60 | 1.ST | 1 | 35 | | | | | 3 | 20 | | | 2 | 5 | 60 | 2 |
| 6 | 60 | 3.ST | | | | | | | | | 1 | 60 | | | 60 | 3 |
| 6 | 60 | 1.ST | 1 | 35 | | | | | 3 | 20 | | | 2 | 5 | 60 | 2 |
| 6 | 60 | 2.ST - a | | | | | 1 | 40 | | | 2 | 20 | | | 60 | 1 |
| 7 | 60 | 3.ST | | | | | | | | | 1 | 60 | | | 60 | 3 |
| 7 | 60 | 1.ST | 1 | 35 | | | | | 3 | 20 | | | 2 | 5 | 60 | 2 |
| 7 | 60 | 2.ST - a | | | | | 1 | 40 | | | 2 | 20 | | | 60 | 2 |
| 1 | 70 | 3.ST | | | | | 1 | 10 | | | 2 | 60 | | | 70 | 1 |
| 2 | 70 | 3.ST | | | | | 1 | 10 | | | 2 | 60 | | | 70 | 1 |
| 3 | 70 | 3.ST | | | | | 1 | 10 | | | 2 | 60 | | | 70 | 1 |
| 4 | 70 | 3.ST | | | | | 1 | 10 | | | 2 | 60 | | | 70 | 3 |
| 4 | 70 | 1.ST | 1 | 35 | | | | | 2 | 20 | 3 | 15 | | | 70 | 1 |
| 5 | 70 | 3.ST | | | | | 1 | 10 | | | 2 | 60 | | | 70 | 3 |
| 5 | 70 | 1.ST | 1 | 35 | | | | | 2 | 20 | 3 | 15 | | | 70 | 2 |
| 6 | 70 | 3.ST | | | | | 1 | 10 | | | 2 | 60 | | | 70 | 3 |
| 6 | 70 | 1.ST | 1 | 35 | | | | | 2 | 20 | 3 | 15 | | | 70 | 2 |
| 6 | 70 | 2.ST | | | | | 1 | 40 | | | 2 | 30 | | | 70 | 1 |
| 7 | 70 | 3.ST | | | | | 1 | 10 | | | 2 | 60 | | | 70 | 3 |
| 7 | 70 | 1.ST | 1 | 35 | | | | | 2 | 20 | 3 | 15 | | | 70 | 2 |
| 7 | 70 | 2.ST - a | | | | | 1 | 40 | | | 2 | 30 | | | 70 | 2 |
| 1 | 80 | 3.ST | | | | | 1 | 20 | | | 2 | 60 | | | 80 | 1 |
| 2 | 80 | 3.ST | | | | | 1 | 20 | | | 2 | 60 | | | 80 | 1 |
| 3 | 80 | 3.ST | | | | | 1 | 20 | | | 2 | 60 | | | 80 | 1 |
| 4 | 80 | 3.ST | | | | | 1 | 20 | | | 2 | 60 | | | 80 | 3 |
| 4 | 80 | 1.ST | 1 | 40 | | | | | 2 | 20 | 3 | 20 | | | 80 | 1 |
| 5 | 80 | 3.ST | | | | | 1 | 20 | | | 2 | 60 | | | 80 | 3 |
| 5 | 80 | 1.ST | 1 | 40 | | | | | 2 | 20 | 3 | 20 | | | 80 | 2 |
| 6 | 80 | 3.ST | | | | | 1 | 20 | | | 2 | 60 | | | 80 | 3 |
| 6 | 80 | 1.ST | 1 | 40 | | | | | 2 | 20 | 3 | 20 | | | 80 | 2 |
| 6 | 80 | 2.ST - a | | | | | 1 | 40 | | | 2 | 40 | | | 80 | 1 |
| 7 | 80 | 3.ST | | | | | 1 | 20 | | | 2 | 60 | | | 80 | 3 |
| 7 | 80 | 1.ST | 1 | 40 | | | | | 2 | 20 | 3 | 20 | | | 80 | 2 |
| 7 | 80 | 2.ST | | | | | 1 | 40 | | | 2 | 40 | | | 80 | 2 |
| 1 | 90 | 3.ST | | | | | 1 | 30 | | | 2 | 60 | | | 90 | 1 |
| 2 | 90 | 3.ST | | | | | 1 | 30 | | | 2 | 60 | | | 90 | 1 |
| 3 | 90 | 3.ST | | | | | 1 | 30 | | | 2 | 60 | | | 90 | 1 |
| 4 | 90 | 3.ST | | | | | 1 | 30 | | | 2 | 60 | | | 90 | 3 |
| 4 | 90 | 1.ST | 1 | 40 | | | | | 2 | 20 | 3 | 30 | | | 90 | 1 |
| 5 | 90 | 3.ST | | | | | 1 | 30 | | | 2 | 60 | | | 90 | 3 |
| 5 | 90 | 1.ST | 1 | 40 | | | | | 2 | 20 | 3 | 30 | | | 90 | 2 |
| 6 | 90 | 3.ST | | | | | 1 | 30 | | | 2 | 60 | | | 90 | 3 |
| 6 | 90 | 1.ST | 1 | 40 | | | | | 2 | 20 | 3 | 30 | | | 90 | 2 |
| 6 | 90 | 2.ST - a | | | | | 1 | 40 | | | 2 | 50 | | | 90 | 1 |
| 7 | 90 | 3.ST | | | | | 1 | 30 | | | 2 | 60 | | | 90 | 3 |
| 7 | 90 | 1.ST | 1 | 40 | | | | | 2 | 20 | 3 | 30 | | | 90 | 2 |
| 7 | 90 | 2.ST - a | | | | | 1 | 40 | | | 2 | 50 | | | 90 | 2 |

Table 15b: Rules for preparing exercise session depending on frequency and time in flexibility strategy (3.ST) - Continued

FIG. 21

METHOD FOR PREPARING A CUSTOMIZED EXERCISE STRATEGY

TECHNICAL FIELD

The present invention relates to a method for preparing and monitoring a customized exercise prescription based on scientific and concrete data and where all of the fitness components are activated, in the field of health-related fitness.

The invention relates to a method for determining a customized exercise strategy and prescription using one's present age- and gender-related physical status and considering all of the health-related fitness components (cardiovascular endurance component, muscular strength component, muscular flexibility component and body composition component), prioritizing them and creating their scope, calculating the intensity and duration of exercises geared towards each component in relation to the total time spent for exercising in addition to the conventional customized exercise preparing methods for achieving the target norms of cardiovascular endurance, muscular strength and flexibility.

BACKGROUND OF THE INVENTION

Today the time devoted to the man himself and to maintain his health is short and it is getting shorter. The diseases resulting from physical inactivity which begin affecting man's health have brought all countries to run campaigns to encourage people to conduct physical activities with the leadership of World Health Organization, and have caused insufficiency of the budgets spent by the countries for health-related expenses and have even become a serious threat for insurance and retirement systems.

FIT letters forming the word fitness indicate the actual meaning of exercise. When Principles of Frequency, Intensity, Time are applied to any physical activity they are converted to exercise and the physical activity must have a purpose. Today, since most people associate fitness with weight control in general, it has become a tradition to prepare an exercise prescription only based on the values of body composition of a person (namely fat ratio, water ratio and fat-free mass of body). Exercise prescription is prepared without taking into account the risk factors (whether that person is sedentary or not, smokes or not, has a positive family history or not, has hyperlipidemia or not, has hypertension or diabetes or obesity) and the measurable fitness components related to actual health of a person (cardiovascular endurance, muscular strength and muscular flexibility)

Basic fitness components are as follows:
Cardiovascular endurance component (maxVO2)
Muscular Strength component
Muscular Flexibility component
Body Composition (fat ratio+fat-free mass) component While preparing a fitness exercise prescription by traditional methods, the importance, ranking, intensity, and the ratio of the time spent for improving each component to total time of exercise are not taken into consideration. In this calculation mostly body composition values are taken into consideration. Besides, body composition measurement devices of different brands may vary in analyzing the data.

Traditional method of exercise prescription is based on body composition information consisting of three types of data. Apart from that, exercises of cardiovascular endurance, muscular strength and muscular flexibility are created without any target and randomly without being based on any concrete data and system.

In the developed method, one's cardiovascular endurance, muscular strength, and muscular flexibility are based on relevant age- and gender-related norms; the comparison of these age- and gender-related norms is considered, and according to the comparison of the measured component results, the priority, scope and frequency of the fitness components are calculated, and the exercise program concerning health is prepared by determining the exercise priority and frequency.

As also stated above, while an exercise prescription which is prepared by the traditional method is only based on the data of body composition, the very necessary healthy and right combination of exercise cannot be obtained since not all of the fitness components are taken into consideration.

As a consequence, due to the negative points explained above and the insufficiency of traditional methods for prescribing exercise programs in health-related fitness, improvement or development of methods for preparing and tracking exercise strategy and prescription is necessary which are different from the known methods.

OBJECTIVES OF THE INVENTION

The objective of the invention is, motivated by the insufficiency of traditional methods, to improve the exercise prescription methods and to resolve the drawbacks of existing methods for preparing and monitoring an exercise strategy and prescription mentioned above.

An objective of the invention is to avoid the wrong exercises within the current system and to prevent injury or death by cross checks and by considering all of the fitness components (cardiovascular endurance, muscular strength, muscular flexibility) and the sub-units of these components which will affect the exercises to be prepared by an instructor and to be provided to candidates who want to do fitness.

Another objective of the invention is to automatically prepare a strategy of right and healthy exercise according to a person's physical components considering the possibility that an instructor may not have all of the knowledge about cross-checking fitness components.

An objective of the invention is to prepare a health-related exercise strategy and prescription by determining and considering the priority, scope and intensity of the fitness components, basing these on norms of cardiovascular endurance, muscular strength and muscular flexibility and considering the comparison of these norms to age and gender.

Another objective of the invention is to prepare the most beneficial exercise prescription for a person.

Another objective of the invention is to determine a detailed order of exercise.

Another main objective of the invention is to determine a personal fitness score.

Structural and characteristic properties of the invention and all of its advantages will be better understood with the help of the figures given below and the detailed description given in reference to these figures, and for this reason the assessment also needs to be performed in consideration of these figures and their detailed description.

FIGURES TO HELP UNDERSTANDING THE INVENTION

FIG. 1, view of health related fitness components in order of importance.

FIG. 2, view of fitness map on the display (screen).

FIG. 3a, view of the state when the score of a fitness component fills the entire space reserved for it in the fitness map.

FIG. 3b, view of the state when the score of a fitness component cannot fill the entire space reserved for it in the map.

FIG. 4, view of the ideal state of fitness components of a person.

FIG. 5, view of the state of fitness components of a person which need to be improved.

FIG. 6, general view of fitness components and sub-components of strength component.

FIG. 7, schematic view of priority in the cardio strategy which comes first among the 3 types of exercise strategy.

FIG. 8, schematic view of priority in the strength strategy which comes second among the 3 types of exercise strategy.

FIG. 9, schematic view of priority in the flexibility strategy which comes third among the 3 types of exercise strategy.

FIG. 10, view of time and frequency in the exercise session. (For example, it is an exercise session performed for 90 minutes a day, 3 days a week.)

FIG. 11 illustrates Table 1: Leading causes of death due to illness in Turkey

FIG. 12 illustrates Table 2: Link between cardiovascular endurance and cardiovascular mortality FIG. 13 illustrates Table 3: Average lifespan of human being according to years FIG. 14 illustrates Table 4: Average lifespan of human being lived healthy and unhealthy FIG. 15 illustrates Table 12: Diagram of rules to determine exercise strategy FIG. 16 illustrates Table 13a) and FIG. 17 illustrates Table 13 b): Rules for preparing exercise session depending on frequency and time in cardio strategy (1.ST)

FIG. 18 illustrates Table 14(a) and FIG. 19 illustrates Table 14(b): Rules for preparing exercise session depending on frequency and time in strength strategy (2.ST)

FIG. 20 illustrates Table 15(a) and FIG. 21 illustrates Table 15(b): Rules for preparing exercise session depending on frequency and time in flexibility strategy (3.ST)

Figure 1:
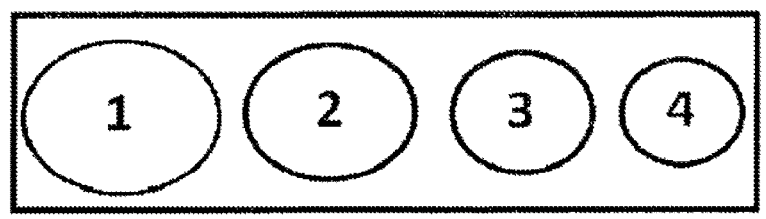
Figure 2:
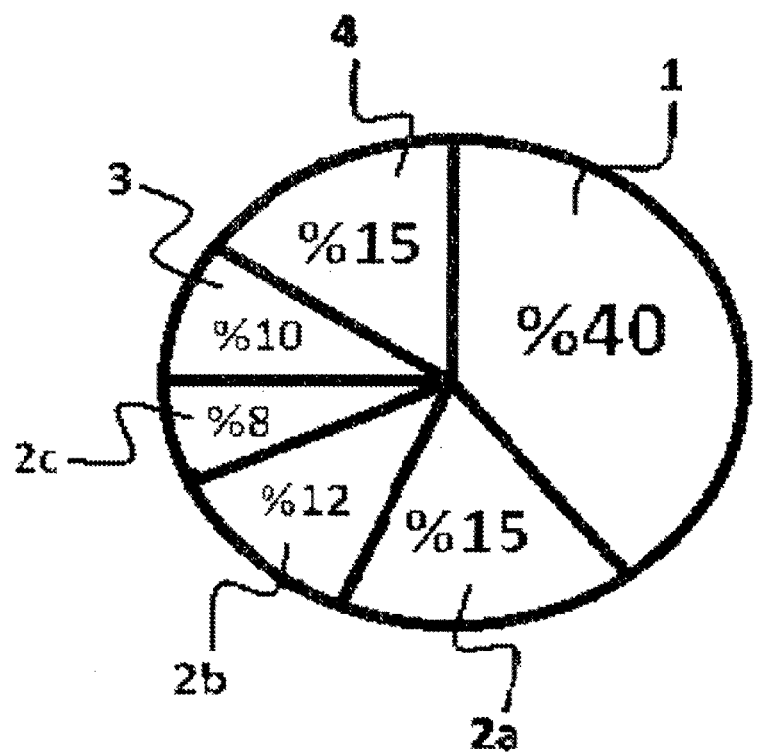

DESCRIPTION OF PART REFERENCES 1. maxVO2 (cardiovascular endurance component, cardiovascular endurance)
2. Muscular strength component (Strength Component, muscular strength)
   2a. Lower Extremity
   2b. Upper Extremity
   2c. Trunk
3. Muscular Flexibility Component
4. Body Composition Component
   Fat-Free Mass Which is Another Component of Body Composition is Comprised of Protein, Mineral and Water.

Drawings do not have to be scaled and unnecessary details which are not required to understand the present invention might have been disregarded. Apart from that, elements which are at least considerably identical or which have at least considerably identical functions are indicated with the same number.

DETAILED DESCRIPTION OF THE INVENTION

In this detailed description, preferred steps of the method according to the invention are described only to help better understand the subject.

A method for preparing and monitoring a customized exercise strategy and prescription based on scientific and concrete data after determining the values of measurable fitness components related to health of a person such as cardiovascular endurance component (1), component of muscular strength(2), component of muscular flexibility (3), body composition component (4) via measurement devices or other methods in the field of health-related fitness characterized in that; in order to improve each fitness component of a person, said method comprises; considering the values of cardiovascular endurance component (1), muscular strength component (2), muscular flexibility component (3), body composition component(4) at a certain percentage, in a total, calculating the ratio of values of a person's fitness components to the age—and gender related norms;

calculating fitness component score separately for each component; calculating weighted total of fitness score based on the scores of all of the fitness components; creation of fitness map image and filling this map according to the said calculations in said method; monitoring the components in the map by determining their ratio within a total and prioritizing them; allocating the biggest ratio to cardiovascular endurance(1) (maxVO2)component, the second biggest ratio to component of muscular strength component, the third biggest ratio to body composition and the fourth biggest ratio to muscular flexibility component in said partition; determining an exercise strategy by putting these components in order, in terms of priority of affecting health via said method in accordance with measurements of fitness components, the said exercise strategy is divided into three as Cardio, Strength and Flexibility Strategy; determining an exercise session which will simultaneously improve the person's fitness components via said method within the frame of the above-said rules and contain the instructional steps within.

With the method subject to the invention a person's body composition (4), cardiovascular. endurance (1), muscular strength (2) from different parts and flexibility level (3) are determined. Depending on the frequency and time that a person will reserve for exercise per week, exercise strategy, exercise time and scope are designated according to objective norms (For example, Table 5, 7, 8, 9, 10 etc.) and concrete rules (Table 12).

In said method for preparing an exercise strategy and prescription: component of strength(2) which is the second among the above-mentioned fitness components is also divided into three separate sub-components (lower extremity strength(2a), upper extremity strength(2b) and trunk strength(2c)). Five different components come up as a result of this division. After obtaining six fitness components by also adding component of body compositions (4) to these five different components, exercise strategies are determined systematically.

In said method for preparing exercise strategy and prescription, in order to improve the relevant fitness components; the structuring of the prepared exercise strategy and thus prescription comprises three main topics:
A) Creating fitness map: identifying component ratios and filling the map according to these ratios; determining the fitness score
B) Preparing exercise strategy
C) Identifying the scope of exercise and program flow depending on exercise frequency and time after identifying the type of strategy First, distribution of fitness components in fitness map is determined on the basis of scientific researches. Afterwards, according to the fitness components' measurements, their relevant degree and their location—in accordance with the norms—are determined, in the space allocated for components, in a whole. In accordance with the determinations for fitness components, three main components (cardiovascular endurance (1) exercises, muscular strength (2) exercises, flexibility (3) exercises) are arranged in order of priority with respect to the importance of their effects to health. With the use of all of the data and factors, an exercise program is determined targeting simultaneous improvement of these components.

A) Creating Fitness Map: Identifying Component Ratios and Filling the Map According to These Ratios; Determining Fitness Score 1. Determination of Fitness Component Ratios in Fitness Map The infrastructure of the map is created in giving a certain percentage (%) ratio, according to the importance of impact on health of each fitness component.

In determining the ratios, international data were considered in. Namely:

In the scientific platform, there are cardiovascular endurance (1), muscular strength (2), muscular flexibility (3) and body composition (4) in the health-related measurable fitness components. These components being closely related to physical health, their measurable nature, their norms depending on age and gender enables monitoring a person's for physical suitability (fitness) objectively. For the concept of health, although there are mental and social health in addition to physical health the leading cause of death is coronary heart disease according to statistics (Table 1). The most important reason of this fact today is obesity and emergence of risk factors such as hyperlipidemia, diabetes, hypertension correspondingly.

When looking at the fitness components, it is possible to state, based on the scientific evidences that the most important component which affects the most important risk factor given above positively is the exercises which increase cardiovascular endurance (Table 2). Because of its contribution being the most important among others, cardiovascular endurance (maxVO2-ml/dk/kg) (1) is given the ratio of 40% which is the biggest share in the fitness map.

According to the scientific evidences, the second most important fitness component related to physical health is muscular strength(2) in today's conditions. The aim is to maintain the muscle mass which constitutes the strength and to enable a person to continue his/her life without being in need of external support by increasing the muscular strength. Average lifespan of a human being was 47 in 1900s and 78 in 2006 (Table 3). According to the statistical data, it is known that during the last 13 years of the 78 years of lifespan a person needs external support (Table 4). The most important reason of this situation is the age related sarcopenia (muscular dystrophy) which emerges as the lifespan of human being gets longer and the fact that the person thus cannot perform the basic vital activities physically. Therefore, ACSM (American College of Sports Medicine) which is one of the most important institutions in the world in the field of exercise puts resistance exercises in the exercise prescription officially in 1998. Based on all these data, lower extremity (2a) is allocated a share of 15%, upper extremity (2b) a share of 12%, trunk (2c) a share of 8% and strength component (2) is therefore allocated a total share of 35%.

The third most important component which serves a function in preparing an exercise strategy and prescription is the flexibility component (3). Today, it is known that flexibility of hind leg and back of a person take an important place since chronic low back pain is very common and it is a factor affecting quality of life. The smallest share at the rate of 10% is allocated to flexibility component (3) because of its role in survival of a person and in physiological actions although it is an important component.

Body composition (4); does not have any effect on the exercise strategy. However, especially since obesity affects health seriously, the share allocated to the body composition (4) is 15% in fitness map. The map mentioned in a preferred embodiment of the invention is a diagram.

2. Method for Filling the Sections in Fitness Map

Relevant fitness components are measured with direct or indirect methods and placed in the map with the following method.

a) Cardiovascular Endurance (max VO2) (1)

With the method subject to the invention, default minimum value of maxVO2 (1) is accepted as zero (0) and default maximum value of maxVO2 (1) is accepted as one hundred (100) according to the norms for age and gender of the person. Thus, the calculated value of maxVO2 falls between 0 and 100, and gives an accurate percentage measure for filling the space allocated to maxVO2 in the fitness map. These processes are formulated by using the method of interpolation as follows:

(Measured value of fitness component−minimum value of fitness component)/(maximum value of fitness component−minimum value of fitness component)*100

EXAMPLE

In Table 5, for a male between ages of 30-34, the values of 29 and lower corresponding to "very poor" state are taken as 0 and the values of 56 and higher corresponding to perfect state indicates 100. If maxVO2 value of a male at the age of 30 is 41.0 ml/min/kg this falls into average class according to the norms. For maxVO2 value of 41.0 ml/min/kg, component score on the scale of 100 is calculated as (41−29)/(56−29)*100=44.44.

TABLE 5

Data of MaxVO2 norms
MaxVO2 NORMS (ml/min/kg)
CLASSIFICATION

| | AGE | VERY POOR | POOR | BELOW AV-ERAGE | AV-ER-AGE | GOOD | VERY GOOD | PER-FECT |
|---|---|---|---|---|---|---|---|---|
| Male | 20-24 | <32 | 32-37 | 38-43 | 44-50 | 51-56 | 57-62 | >62 |
| | 25-29 | <31 | 31-35 | 36-42 | 43-48 | 49-53 | 54-59 | >59 |
| | 30-34 | <29 | 29-34 | 35-40 | 41-45 | 46-51 | 52-56 | >56 |
| | 35-39 | <28 | 28-32 | 33-38 | 39-43 | 44-48 | 49-54 | >54 |
| | 40-44 | <26 | 26-31 | 32-35 | 36-41 | 42-46 | 47-51 | >51 |
| | 45-49 | <25 | 25-29 | 30-34 | 35-39 | 40-43 | 44-48 | >48 |
| | 50-54 | <24 | 24-27 | 28-32 | 33-36 | 37-41 | 42-46 | >46 |
| | 55-59 | <22 | 22-26 | 27-30 | 31-34 | 35-39 | 40-43 | >43 |
| | 60-65 | <21 | 21-24 | 25-28 | 29-32 | 33-36 | 37-40 | >40 |

Source: Shvartz E, Reibold RC: Aerobic fitness norms for males and females aged 6 to 75 years: a review. Aviat Space Environ Med; 61: 3-11, 1990.

Figures 3A, 3B:
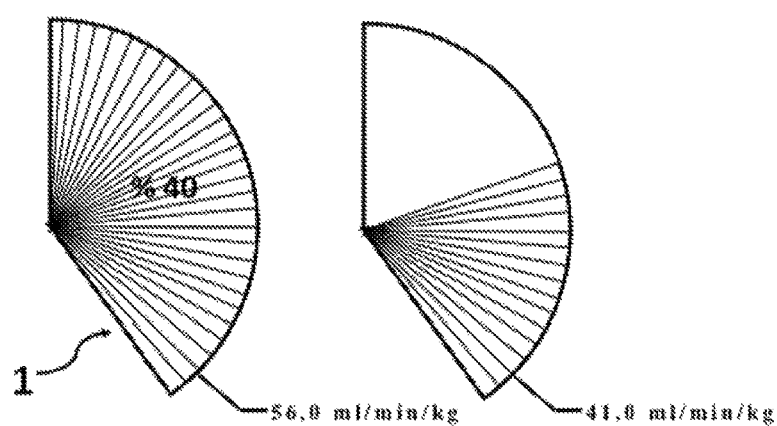

From this example on, maxVO2 (1) section of the person in this example is given with a view in the map in FIG. 3b.

As maxVO2 (1) value of a person increases the map section allocated to cardiovascular endurance which corresponds to 40% of the whole map gets more and more filled. Accurate monitoring of a person's improvement is provided according to these map results.

The same route is followed also for other fitness components available in the map and hence monitoring of all of the fitness components is ensured.

After measurements are positioned for each fitness component, the fitness score is calculated on the scale of 100 (Table 6) and a person's total fitness score is obtained by this way based on all of the fitness components.

When a few different areas within a particular area are measured, their average is taken into consideration. As strength component (2) is divided into three different components (2a, 2b, 2c), there are many different tests to determine the level of each sub-component. Therefore, for instance, if two different tests are performed to determine upper extremity (2b) level, the results of both tests are taken and their average is displayed in the map.

TABLE 6

Sample of fitness score for a male at the age of 30 who has average levels of measurement in each fitness component

| All the Fitness components | Fitness component multiplier (weight) | Component Score (male min.) | Component score (male max.) | Male min. | Male max. |
|---|---|---|---|---|---|
| maxVO2 | 0.40 | 44.44 | 59.26 | 17.78 | 23.70 |
| lower extremity (e.g. leg press) | 0.15 | 17.95 | 32.05 | 2.69 | 4.81 |
| upper extremity (e.g. bench press) | 0.12 | 22.86 | 34.29 | 2.74 | 4.11 |
| trunk (e.g. pull-up with knees bent) | 0.08 | 40.00 | 60.00 | 3.20 | 4.80 |
| flexibility | 0.10 | 37.50 | 62.50 | 3.75 | 6.25 |
| body composition | 0.15 | 100.00 | 75.00 | 15.00 | 11.25 |
| FITNESS SCORE | | | | 45.16 | 54.93 |

After finding out the fullness percentage(occupancy) of 6 different components (including sub-components of strength component(2)) in the related spaces allocated for each, the occupancy on the whole map(namely 100%) of total's sum, is determined on the same and single map. This result is the fitness score. The reason for obtaining fitness score is to see which fitness component is in which state and how fit a person is. The calculations of fitness score exemplified above, can be generalized as weighted sum of the scores of all the fitness components with the following mathematical expression.

$$\sum_{i=Fitness\ component} Component\ weight_i * Component\ score_i$$

Since the component scores are calculated by interpolation this formulation can be stated as follows:

$$\sum_{i=Fitness\ component} Component\ weight_i * \frac{(Measured\ value_i - Minimum\ value_i)}{(Maximum\ value_i - Minimum\ value_i)} * 100$$

TABLE 7

LOWER EXTREMITY STRENGTH NORMS (leg press)

| | AGE | VERY POOR | POOR | AVERAGE | GOOD | VERY GOOD | EXCELLENT |
|---|---|---|---|---|---|---|---|
| Male | ≤20 | ≤1.56 | 1.57-1.79 | 1.80-1.92 | 1.93-2.09 | 2.10-2.82 | >2.82 |
| | 20-29 | ≤1.50 | 1.51-1.67 | 1.68-1.86 | 1.87-2.00 | 2.01-2.40 | >2.40 |
| | 30-39 | ≤1.42 | 1.43-1.55 | 1.56-1.67 | 1.68-1.80 | 1.81-2.20 | >2.20 |
| | 40-49 | ≤1.34 | 1.35-1.47 | 1.48-1.58 | 1.59-1.70 | 1.71-2.02 | >2.02 |
| | 50-59 | ≤1.21 | 1.22-1.35 | 1.36-1.49 | 1.50-1.60 | 1.61-1.90 | >1.90 |
| | 60+ | ≤1.15 | 1.16-1.26 | 1.27-1.39 | 1.40-1.51 | 1.52-1.80 | >1.80 |

Source: Institute for Aerobics Research, Dallas, TX, 1994

TABLE 8

UPPER EXTREMITY STRENGTH NORMS (bench press) CLASSIFICATION

| | AGE | VERY POOR | POOR | EXCELLENT | GOOD | VERY GOOD | EXCELLENT |
|---|---|---|---|---|---|---|---|
| Male | ≤20 | ≤0.76 | 0.77-0.92 | 0.93-1.09 | 1.10-1.22 | 1.23-1.76 | >1.76 |
| | 20-29 | ≤0.72 | 0.73-0.89 | 0.90-1.02 | 1.03-1.17 | 1.18-1.63 | >1.63 |
| | 30-39 | ≤0.65 | 0.66-0.80 | 0.81-0.89 | 0.90-1.00 | 1.01-1.35 | >1.35 |
| | 40-49 | ≤0.59 | 0.60-073 | 0.74-0.81 | 0.82-0.89 | 0.90-1.20 | >1.20 |
| | 50-59 | ≤0.53 | 0.54-0.65 | 0.66-0.72 | 0.73-0.80 | 0.81-1.05 | >1.05 |
| | 60+ | ≤0.49 | 0.50-0.59 | 060-0.66 | 0.67-0.73 | 0.74-0.94 | >0.94 |

Source: Institute for Aerobics Research. Dallas, TX. 1994

TABLE 9

TRUNK STRENGTH NORMS (1' pull-up with knees bent)
CLASSIFICATION

| | AGE | POOR | BELOW AVERAGE | AVERAGE | GOOD | VERY GOOD |
|---|---|---|---|---|---|---|
| Male | 15-19 | ≤32 | 33-37 | 38-41 | 42-47 | ≥48 |
| | 20-29 | ≤28 | 29-32 | 33-36 | 37-42 | ≥43 |
| | 30-39 | ≤21 | 22-26 | 27-30 | 31-35 | ≥36 |
| | 40-49 | ≤16 | 17-21 | 22-25 | 26-30 | ≥31 |
| | 50-59 | ≤12 | 13-17 | 18-21 | 22-25 | ≥26 |
| | 60-69 | ≤6 | 07-11 | 12-16 | 17-22 | ≥23 |

Source: The Canadian Physical activity. Fitness & Lifestyle Appraisal: CSEP's Plan for Healthy Active Living, 1996

TABLE 10

FLEXIBILITY (Sit & Reach) NORMS
CLASSIFICATION

| | AGE | POOR | BELOW AVERAGE | AVERAGE | GOOD | VERY GOOD |
|---|---|---|---|---|---|---|
| Male | 15-19 | ≤23 | 24-28 | 29-33 | 34-38 | ≥39 |
| | 20-29 | ≤24 | 25-29 | 30-33 | 34-39 | ≥40 |
| | 30-39 | ≤22 | 23-27 | 28-32 | 33-37 | ≥38 |
| | 40-49 | ≤17 | 18-23 | 24-28 | 29-34 | ≥35 |
| | 50-59 | ≤15 | 16-23 | 24-27 | 28-34 | ≥35 |
| | 60-69 | ≤14 | 15-19 | 20-24 | 25-32 | ≥33 |

Source: Institute for Aerobics Research. Dallas. TX. 1994

TABLE 11

BODY COMPOSITION (fat percentage-ratio) NORMS
CLASSIFICATION

| | AGE | VERY LOW | LOW | NORMAL | HIGH | VERY HIGH |
|---|---|---|---|---|---|---|
| Male | 20-29 | <7 | 7-9 | 10-19 | 20-25 | >25 |
| | 30-39 | <8 | 8-13 | 14-22 | 23-27 | >27 |
| | 40-49 | <9 | 9-16 | 17-24 | 25-29 | >29 |
| | 50-59 | <10 | 10-18 | 19-25 | 26-30 | >30 |
| | 60+ | <11 | 11-19 | 20-26 | 27-31 | >31 |

Source: WHO (World Health Organization)

b) Calculating Body Composition Component Score

Unlike the other components, as values of body composition (4) increase, human health is affected negatively. Therefore, body composition (4) component score of high fat ratios is zero (0). Values falling between essential fat ratios (3% for men and 12% for women) and lower norm limits for normal (healthy) classification by the World Health Organization are given a score of 100. A decrease of a person's fat ratio below the essential fat ratio is also unfavorable and expert advice is required in such situations. So, component score is seventy five (75) for rates below the essential fat rate. For other fat ratios, component scores are calculated as follows:

Body composition component score =

$$\begin{cases} 75 & \text{Ratio} < \text{Essential value} \\ 100 & \text{Essential value} \leq \text{Ratio} \leq MNNV \\ 75 + 25 * \dfrac{(MXNV - \text{Ratio})}{(MXNV - MNNV)} & MNNV \leq \text{Ratio} \leq MXNV \\ 75 * \dfrac{(\text{Maximum} - \text{Ratio})}{(\text{Maximum} - MXNV)} & MXNV \leq \text{Ratio} \leq \text{Maximum} \\ 0 & \text{Maximum} \leq \text{Ratio} \end{cases}$$

where
$MNNV$: Minimum normal value
$MXNV$: Maximum normal value

For instance, the minimum normal value (MNNV) to be used in the formulation above for a male at the age of 30 is 14 while the maximum normal value (MXNV) is 22 and the maximum value is 27. Ratio is the measured fat rate of a person. Therefore, for a person whose fat ratio is 22 (22%), the component score is 75. Namely, as the weight of body composition (4) is 15 (15%), 75 percent (75%) of the body composition (4) component which has a section of 15 percent in the fitness map is filled. If the fat ratio of a person is 25 (25%), the component score is calculated as 75*(27-25)/(27-22)=30. In such situation 30 percent of the section of 15 percent becomes filled.

As to be explained in more detail under exercise strategy topic, the share taken by measurement of each fitness component in the map actually determines the customized exercise strategy as well. Thus, the share of a component in the map also decides whether that component has priority in the exercise strategy. In the traditional methods for determining exercise, criterion of priority is not evaluated for fitness components and the order is not made according to the objective criteria and concrete data. Cardiovascular exercises, strength exercises and flexibility exercises are applied randomly When all of the fitness components calculated with the above-mentioned methods are put in the sections allocated to them after being compared in accordance with the norms, it enables obtaining concrete data in respect of which component a person needs to improve to what extent.

Figure 4:
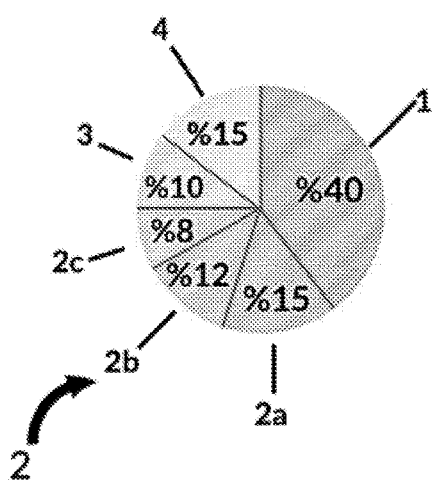
Figure 5:
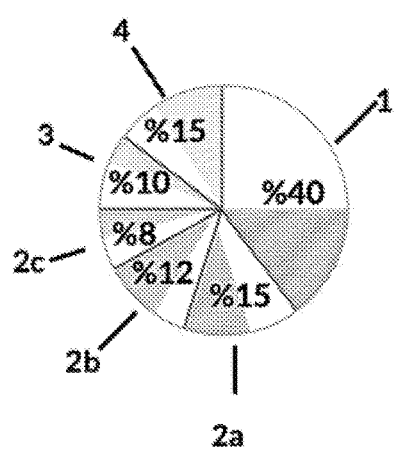
Figure 6:
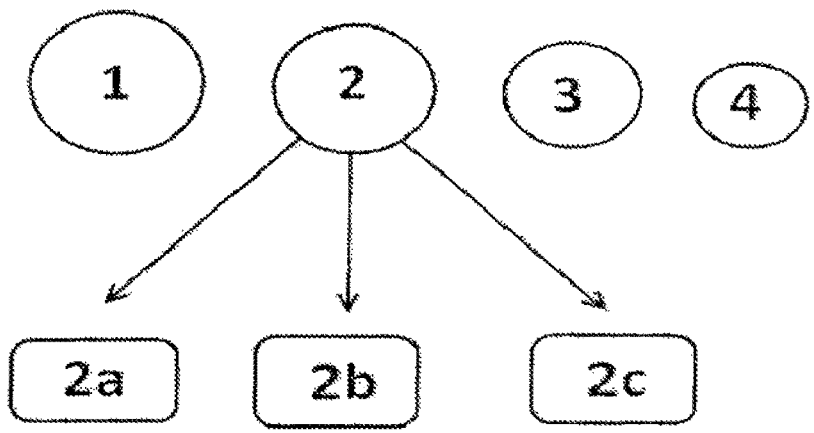

While the state of a person's physical suitability is concretely understood from the fact that the sections of health related fitness components are full (FIG. 4). Another aim of the sections divided according to the priority of different components is to create and monitor simultaneous program for the targets determined in accordance with the map result. Also measurements are kept in the system database at certain time intervals.

As the personal data evaluated according to the norms at regular intervals improve, occupancy of the relevant section in the map increases. Exercise strategy and prescription to be applied varies accordingly. Exercise strategy and consequently prescription are determined according to the ratios of data resulting by interaction of six different components which enable monitoring of personal fitness map subject to invention.

In the developed method, three different main fitness components (cardiovascular endurance (1), muscular strength(2), muscular flexibility (3)) and also muscular strength(2) are evaluated in also three different sub-components (lower extremity (2a) strength, upper extremity (2b) strength and trunk (2c) strength) for preparing exercise strategy and prescription, and with the addition of body composition to all of these components, the exercise strategy according to the present invention is created according to six different components in total. Body composition remains passive in the method of creating exercise. In FIG. 4, distribution of components in their six-chamber sections are shown.

B) Preparing Exercise Strategy

In consideration of the data for health related fitness components in the fitness map (except for body composition (4)), order of priority is determined as explained above.

1. Cardiovascular endurance (maxVO2) (1)
2. Muscular strength(2)
   a-lower extremity (2a)
   b-upper extremity (2b)
   c-trunk (2c)
3. Muscular Flexibility (3)

The way how the rules for creating exercise strategy work is determined as follows:

In order to provide a healthy and proportional physical development of a person, the aim is achieving the 50% of the allocated space for each component in the map by referring to the norms, first of all.

Rules Determining Exercise Strategy (Table 12):
1. maxVO2 (1) value of a person needs to be lower than the half of the space allocated to maxVO2 (1) (<50%) in the map in order to select a cardio strategy. Once these conditions are met, exercise recipe is prepared according to this strategy.
2. If the average of strength components (2) of a person is lower than the half of the space allocated to it (<50%) in the map and at the same time maxVO2 (1) value of the person needs to be higher than the half of the space allocated to maxVO2 (1) (>50%) in order to select a strength strategy. Once these conditions are met, exercise recipe is prepared according to strength strategy.
   a. In the exercise strategy where strength component (2) has priority, strength components (2) are evaluated separately and order is calculated accordingly. However, lower extremity (2a) from strength components (2) is not put consecutively in cardiovascular exercises.
3. If the value of flexibility components (3) of a person is lower than the half of the space allocated to flexibility (<50%) and at the same time maxVO2 (1) value and strength(2) value of the person need to be higher than the half of the space allocated to them (>50%) in order to select a flexibility strategy. Once the relevant conditions are met, exercise recipe is prepared according to flexibility strategy.
4. If body composition (4) exceeds the limit in terms of fat rate, medical support (dietary program etc.) is recommended. Body composition (4) component does not have any effect in the determination of exercise strategy.
5. After components first reach 50% of the spaces allocated to them, the same route is followed to enable reaching 75% and then 100% in consideration of the conditions in the same way.

Figure 7:
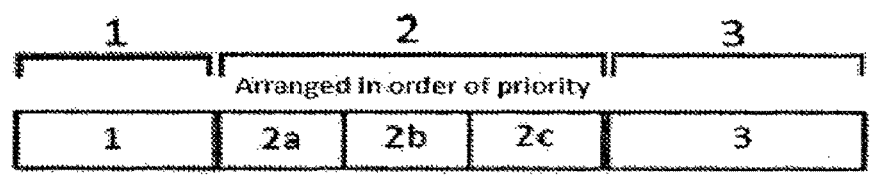
Figure 8:
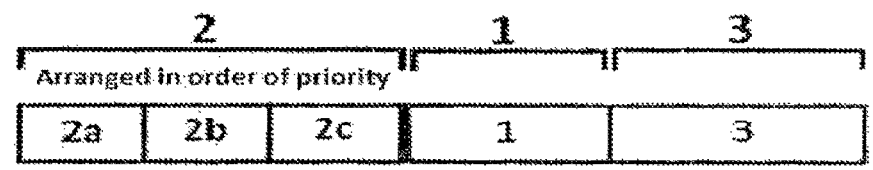
Figure 9:
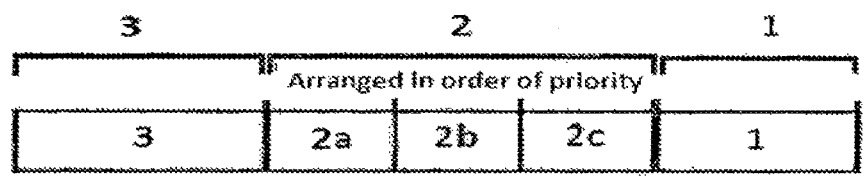
Figure 14:
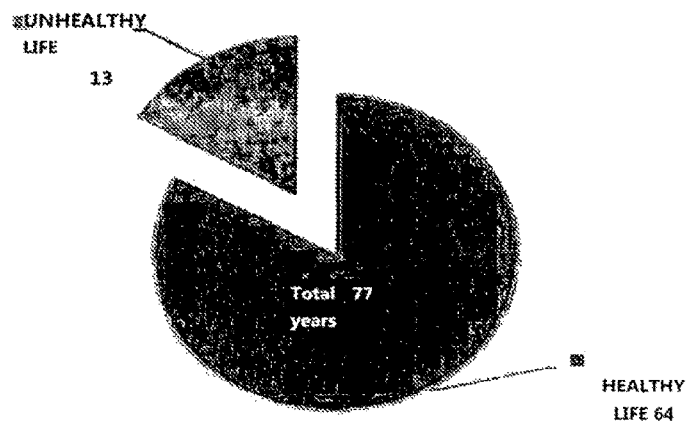
Figure 15:
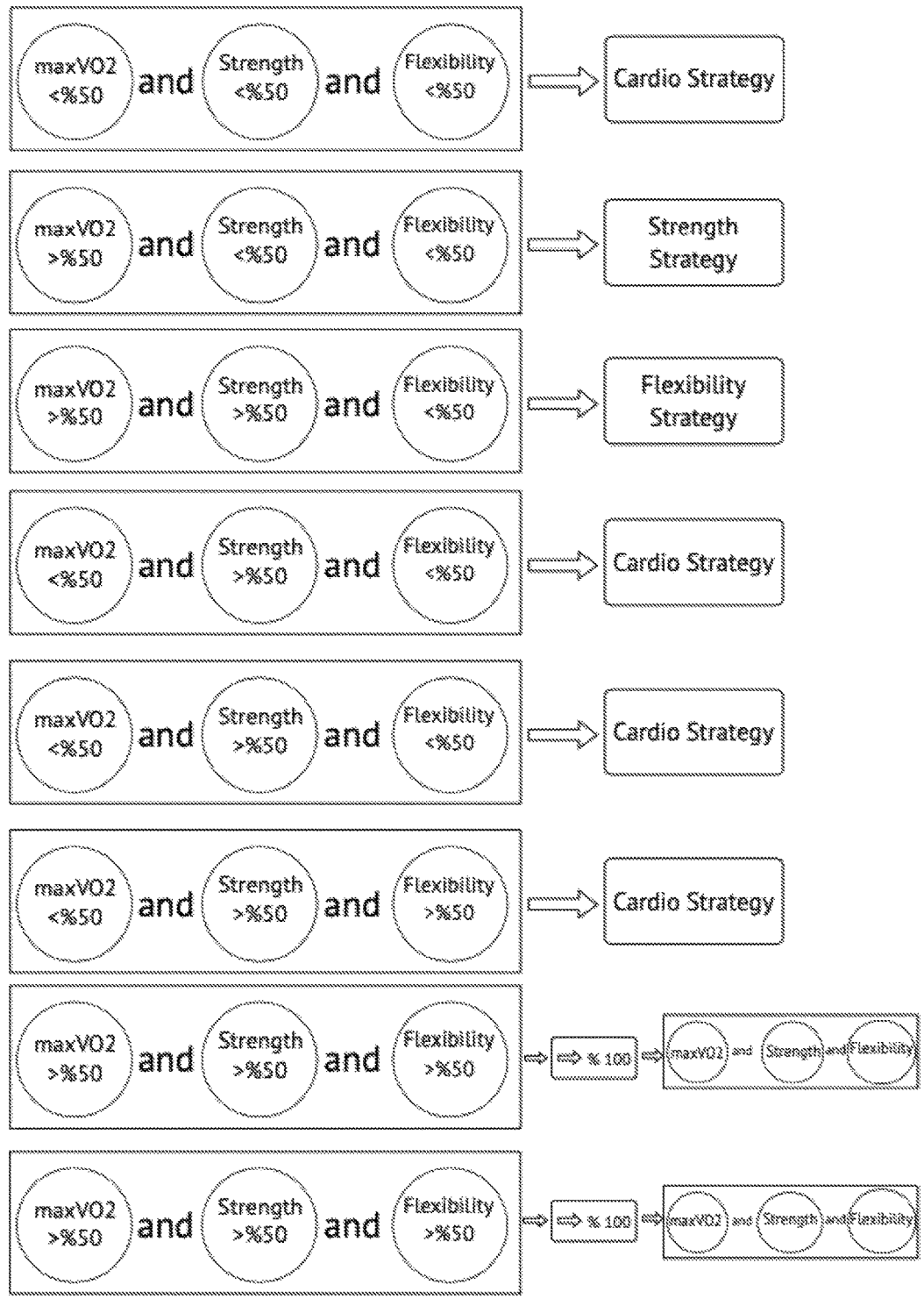

According to these conditions, a total of three different exercise strategies are prepared on customized basis (FIG. 7, FIG. 8, FIG. 9).

C) Identifying the Scope and Flow of Exercise Depending on Exercise Frequency and Time for Each Exercise Session After Identifying the Type of Strategy Determination of exercise program and its rules for the improvement of fitness components according to the frequency and time spared for exercise for each exercise session:

At the same time, in the exercise strategy: with the purpose of determining the detailed order of exercise, in order to put forth the differences of components in terms of aim and intensity, each component is divided into two and a new terminology is created as follows:
   Cardio component as "PRIMARY CARDIO" and "SECONDARY CARDIO";
   Strength component as "PRIMARY STRENGTH" and "SECONDARY STRENGTH";
   Flexibility component as "PRIMARY FLEXIBILITY" and "SECONDARY FLEXIBILITY".

As strength component consists of three different sub-components (lower extremity, upper extremity and trunk), average value of three components are considered in. These values are not considered in the traditional method for calculating fitness exercise.

Depending on the frequency (1, 2, 3, 4, 5, 6, 7) and time (30', 40', 50', 60', 70', 80', 90') which can be spared for exercise, it is determined how much time and which frequency will be spared for which fitness component in each exercise session (FIG. 10).

Before describing the general rules applied for this determination and the operating principles of components, some of the terms found in the description of the method for preparing strategy and prescription of fitness exercise according to the present invention are given below:
1. PRIMARY CARDIO
2. SECONDARY CARDIO
3. PRIMARY STRENGTH
4. SECONDARY STRENGTH
5. PRIMARY FLEXIBILITY
6. SECONDARY FLEXIBILITY The importance of priority rule in respect of fitness components is great. There are three different sources of energy in human body physiologically. The one with the lowest rate of presence in our bodies is the source of carbohydrate. For example, in the body of a person with a weight of 70 kg and a fat rate of 14%, there is a source of energy with 88200 kcal from fat and approximately 2000 kcal from carbohydrate. Therefore, when it is considered that time of exercise also depends on these sources of energy, it is not possible to improve all of the fitness components simultaneously and equally in an exercise session in terms of energy system.

The fact that it is impossible for all of the components to operate in full performance in the same session in terms of both time and energy, makes the development of objective strategies based on the data available in respect of the priority and order of fitness components (negative effects caused to the performance of each other) necessary.

The frequency and scope that AGSM, which is one of the most important institutions in the world in the field of exercise, recommends are as follows:
   With respect to cardiovascular endurance (1); 3-7/days a week; 20-60 minutes,
   With respect to muscular strength(2); 2-3/days a week; at least 1 set (8-12 RM) of 8-10 exercises,
   With respect to flexibility (3); exercises of at least 15 minutes with 15-30 second breaks during 4 sets.

Keeping in mind that the primary aim of the exercise is to reach health, it is obvious that it is important to manage time spared for exercise in order to contribute to health by way of exercise. From this point on, the developed method for creating strategy and exercise prescription is actually based on the logic of granting priority in terms of both fitness components and sub-components of strength components (2) and administered with certain rules. Thus, the need for applying each fitness component in PRIMARY and SECONDARY degrees comes up. According to the strategy determined by using these terms, the duty of enabling reaching the primary aim lies on "PRIMARY" type while "SECONDARY" type is applied for maintaining purposes when there is increase in the opportunities of time and frequency.

Description of Terms:

1. Primary Cardio:
   a) In terms of intensity of exercise, (provided that there is no limitation with regard to the risk factors of the person) upper limit may extend to 85% of maxVO2 (1).
   b) It is applied to the situation where cardiovascular endurance has priority.
   c) Its primary aim is to improve the cardiovascular endurance (1) of the person.

2. Secondary Cardio:
   a) In terms of intensity of exercise, upper limit may extend to 60% of maxVO2 (1).
   b) It is applied to the strategies where cardiovascular endurance does not have priority.
   c) It always precedes the secondary flexibility.
   d) Its primary aim is to provide energy consumption in aerobic environment.

3. Primary Strength:
   a) In terms of intensity of exercise, 6 repetition maximum (RM) are applied corresponding to the upper limit of 85%.
   b) It is applied to the situations where muscular strength (2) has priority.
   c) Its primary aim is to improve STRENGTH.

4. Secondary Strength:
   a) In terms of intensity of exercise, 10 RM (repetition maximum) are utilized corresponding to the upper limit of 75%.
   b) It is applied to the situations where muscular strength (2) does not have priority.
   c) Its primary aim is to maintain strength.

5. Primary Flexibility:
   a) In terms of scope of exercise, it is used to improve flexibility of joints of human body.
   b) It is applied to the situations where flexibility has priority.
   c) Meaning of its scope is minimum 30 minutes per session.

6. Secondary Flexibility:
   a) In terms of scope of exercise, it is applied to let the muscles get into their former shape (pre-exercise shape) at the end of exercises which affect muscular flexibility (3) negatively (e.g.: especially cardiovascular exercises where movement area of muscles of legs is limited).
   b) It is applied definitely after cardio exercises.
   c) Meaning of scope is minimum 5 and maximum 10 minutes.

General Rules and Operating Principles of Components Applied for Exercise Sessions:

a) In a session where Primary Cardio is applied, Primary Strength Exercises cannot be performed.
      Cardiovascular exercises are the exercises performed to improve cardiovascular, circulatory and respiratory systems. Therefore, the primary aim of the method for preparing health-related strategy and exercise prescription is to eliminate the risk factors which cause coronary heart diseases. The reason of why these kinds of exercises strengthen cardiovascular and circulatory systems is the operation of muscles of legs used during these exercises. It is important to emphasize that heart gains strength by being exposed to pressurized blood from legs and our functional capacity depends on this action. These exercises are the exercises where energy consumption reaches the highest levels among the health related fitness components. Accordingly, due to the decrease in the source of energy in the body and especially the prostration of muscles of legs, the new method does not comprise strength(2) exercises (PRIMARY STRENGTH) of high intensity following cardiovascular (1) exercises (PRIMARY CARDIO). However, there are resistance exercises of lower intensity (SECONDARY STRENGTH) in order to maintain the muscle strength and to provide "stimulus" to muscles.
   b) In the sessions where Primary and Secondary Cardio are applied, flexibility exercises are performed, Secondary flexibility is applied if the time spared for flexibility exercise is up to 10 minutes or Primary Flexibility is applied if it is longer than 10 minutes.
      In the course of cardiovascular exercises, flexibility of muscles and joints are affected negatively in the long term unless flexibility exercises are performed after cardiovascular exercises because especially the joints of hips and knees use a short angle of their range of motion. Flexibility exercises need to be performed in order to prevent these joints from losing their flexibility and to enable muscles of legs to get into their pre-exercise shape. Flexibility exercise (SECONDARY FLEXIBILITY) to be performed for less than 10 minutes depending on the time spared for flexibility (3) is for bringing the muscles into their former (pre-exercise) shape. In accordance with the strategy and the time of session, flexibility (PRIMARY FLEXIBILITY) exercises are performed in order to improve the flexibility of joints for more than 10 minutes.
      Since cardiovascular (SECONDARY CARDIO) exercises not suitable for improvement are to be performed after strength exercises, SECONDARY FLEXIBILITY is performed in order to bring the muscles into their former shape after the exercise.
   c) In the session where Primary Strength is performed, Primary Cardio exercises are not performed.
      This rule used in the method according to the invention is a rule created in the same logic as explained in the "a" paragraph, 7th line, (page 16). Improving muscular strength (2) is one of the most important investments made to maintain health and life quality of human being. The increase in strength depends on the principle of over loading performed with resistance exercises. In short, it is a process performed by leaving muscle under a load which it cannot bear and to cause muscle to renew itself with an increasing protein synthesis. When consider the basic muscle groups (legs, hips, back, chest, shoulders, forearms, triceps, abdomen, waist etc.); it is possible to state that an exercise performed to increase strength requires a significant time. The time spared in such exercises, due to the energy consumed and exercises of high intensity in relation with muscles of legs, PRIMARY CARDIO exercise primary aim of which is to improve cardiovascular endurance is not included following PRIMARY STRENGTH primary aim of which is to improve strength. However, according to the strategy and time of session, in the sessions where PRIMARY STRENGTH is performed, SECONDARY CARDIO exercises performed in low or moderate intensity may be included in order to provide energy consumption.

As strength (2) exercises, especially open kinetic chain resistance exercises do not affect flexibility of joints negatively; flexibility exercise is not a must in the sessions containing strength exercises.

d) Primary Cardio, Secondary Cardio, Primary Strength or Secondary Strength Exercises are never performed after Primary Flexibility.

Primary aim of flexibility (3) exercises is to increase the flexibility of joints. For this aim, they are the exercises performed with plan and knowledge by using FIT principles (frequency, intensity and time). For this reason, there is the rule set as no exercise is performed to reduce the effect or performance of exercise afterwards.

Strategy of exercise (Cardio-Strength-Flexibility) which is selected in accordance with the measurement results and the locations of fitness components on the map, prioritizes the improvement of the fitness component in its target. However, when frequency and time factors are considered in and these factors are at their upper limits, the programs in which other fitness components have priority can also be applied alternatively. For instance, even in the situations where cardio strategy is selected with priority, if a person can spare 7 days a week for exercise, sessions from other strategies may also be applied in certain days of a week.

The Rules for Preparing Exercise Session Depending on Frequency and Time in the Cardio Strategy (I.ST):

a. For the selections up to 3 frequencies, Primary Cardio exercises are applied.
b. For the programs with 4-6 frequencies, Secondary Cardio exercises are applied in the sessions which contain Primary Strength as these sessions provide priority also to strength components.
c. At 1, 2 and 3 frequencies, Strength Component is applied as Secondary Strength. When 4, 5 and 6 frequencies are reached and Secondary Strategy is included, strength component is applied as Primary Strength.
d. At the frequencies over 3, the second and the third strategies as well as the first strategies are put into use in the following systematics.
e. In the exercises with 3 frequencies, the first strategy is applied at each of three frequencies, (3×I.ST)
f. In the exercises with 4 frequencies (3×1. ST)+(1×2.ST)
g. In the exercises with 5 frequencies (3×1. ST)+(2×2.ST)
h. In the exercises with 6 frequencies (3×1. ST)+(2× 2.ST)+(1×3. ST)
i. In the exercises with 7 frequencies (3×1. ST)+(2× 2.ST)+(2×3.ST)

The Rules for Preparing Exercise Session Depending on Frequency and Time in Strength Strategy (2.ST):

a) As strength component (2) is divided into three sub-groups, (lower extremity (2a), upper extremity (2b) and trunk (2c)) it is included as Primary Strength in the programs with 1, 2, 3, 4, 5 and 6 frequencies.
b) In the exercises up to 3 frequencies, as Strength Strategy (2. ST) the weakest one in all of the three different areas is assigned as having the first priority, the area of 1st priority is applied first, the area of 2nd priority is applied second and the area of 3rd priority is applied third. (2. ST-a).
c) In the exercises with 4 frequencies, the area of 2nd priority ranks first, the area of 1st priority ranks second and the area of 3rd priority ranks third in addition to 2.ST-a as Strength Strategy (2. ST-b).
d) In the exercises with 5 and 6 frequencies, the area of 3rd priority ranks first, the area of 1st priority ranks second and the area of 2nd priority ranks third in addition to 2.ST-a and 2.ST-b as Strength Strategy (2.ST-c).
e) In the exercises with 7 frequencies, three strategies (together with a, b, c items of Strength Strategy) are put into use together in the following systematics.
f) At the time intervals of 30', 40' and 50' minutes, the other two strategies as well as the Strength Strategy in 3 and higher frequencies are put into use in the following systematics.
g) In the exercises with 1 frequency (1×2.ST-a)
h) In the exercises with 2 frequencies (2×2.ST-a)
i) In the exercises with 3 frequencies (2×2.ST-a)+(1× 1.ST)
j) In the exercises with 4 frequencies (2×2.ST-a)+(1× 2.ST-b)+(1×1.ST)
k) In the exercises with 5 frequencies (1×2.ST-a)+(1× 2.ST-b)+(1×2.ST-c)+(2×1.ST)
l) In the exercises with 6 frequencies (2×2.ST-a)+(1× 2.ST-b)+(1×2.ST-c)+(2×1.ST)
m) In the exercises with 7 frequencies (2×2.ST-a)+(1× 2.ST-b)+(1×2.ST-c)+(2×1.ST)+(1×3.ST)
n) In the exercises of 60', 70', 80 and 90' minutes, however, the 3rd Strategy is utilized only during the session with 7 frequencies since sessions take longer times, and it runs in the following systematics.
o) In the exercises with 1 frequency (1×2.ST-a)
p) In the exercises with 2 frequencies (2×2.ST-a)
q) In the exercises with 3 frequencies (3×2.ST-a)
r) In the exercises with 4 frequencies (2×2.ST-a)+(2× 2.ST-b)
s) In the exercises with 5 frequencies (2×2.ST-a)+(2× 2.ST-b)+(1×2.ST-c)
t) In the exercises with 6 frequencies (2×2.ST-a)+(2× 2.ST-b)+(2×2.ST-c)
u) In the exercises with 7 frequencies (2×2.ST-a)+(2× 2.ST-b)+(2×2.ST-c)+(1×3.ST)

The Rules for Preparing Exercise Session Depending on Frequency and Time in Flexibility Strategy (3.ST):

a) Secondary Cardio exercise is not present.
b) At 4 and higher frequencies, the first strategy as well as the third strategy is utilized in the following systematics.
c) At 6 and higher frequencies, the second strategy as well as the third and the first strategies is utilized in the following systematics.
d) In the exercises with 1 frequency (1×3.ST)
e) In the exercises with 2 frequencies (2×3.ST)
f) In the exercises with 3 frequencies (3×3.ST)
g) In the exercises with 4 frequencies (3×3.ST)+(1×1.ST)
h) In the exercises with 5 frequencies (3×3.ST)+(2×1.ST)
1) In the exercises with 6 frequencies (3×3.ST)+(2× 1.ST)+(1×2.ST)
j) In the exercises with 7 frequencies (3×3.ST)+(2×1.ST)+ (2×2.ST)

The ordering in the Strength Strategy is taken as reference in order to appoint the priorities of sub-components in Strength Strategies (2.ST) which are applied in the first and third strategies.

The invention claimed is:
1. A method in the field of health-related fitness for preparing, administering and monitoring a customized exer- cise strategy and prescription based on scientific and concrete data pertaining to a person's health, the method comprising the following steps: measuring, by measuring devices, the person's following fitness components: a cardiovascular endurance component; a muscular strength component; a muscular flexibility component; and a body composition component; calculating each of the aforementioned fitness component values as percentage ratios of the person's total fitness score; calculating weighted percentage ratios and fitness component scores separately for each of the person's fitness component values based on age and gender-related fitness component norms; calculating a weighted total fitness score based on the scores of all of the fitness components; generating and displaying a graphical fitness map, the graphical fitness map comprising and graphically representing the ratios of the calculated fitness components; whereby preparing and monitoring the customized exercise strategy comprises, with the use of software executed on a suitable system and the graphical fitness map: prioritizing the ratios of the fitness components in the customized exercise strategy as follows: allocating the largest ratio to exercises relating to the cardiovascular endurance component; the second largest ratio to exercises relating to the muscular strength component; the third largest ratio to exercises relating to the body composition component; and the fourth largest ratio to exercises relating to the muscular flexibility component; determining an exercise strategy in accordance with measurements of the person's fitness components, the weighted total fitness score and the priority of the fitness components; dividing said exercise strategy into exercises in the fields of improving cardio components, strength components and flexibility components, each component and fitness exercise divided into a further primary and secondary component; determining, based on the further primary and secondary components of each of the fitness components, a detailed order of exercises in each of the fields and for each of the fitness components; and preparing a person's customized exercise strategy based on the determined exercise strategy, the person's customized exercise strategy depending on the frequency and time, which can be spared by the person for exercise, and comprising an order of exercises to be performed; and administering the person's customized exercise strategy.

2. The method of claim 1, wherein:
the method realizes the process steps of calculating the ratio of said fitness component values according to age- and gender-related fitness component values and filling the fitness map according to these ratios by software executed on a system;
the sum of the measured fitness components is determined to be 100%, of which a share of percentage is given to each fitness component in terms of the importance of their effect to health, based on the norms set for age and gender;
allocating the largest share of percentage of the mentioned in the fitness map to cardiovascular endurance at 40%, the second largest share of percentage to muscular strength at 35%, the third largest share of percentage to body composition at 15% and the fourth largest share of percentage to flexibility at 10%;
calculating a component score of each component and determining the occupancy ratio of each component in the space allocated to it in the map;
displaying said fitness component levels in the graphical fitness map in accordance with said ratios; and
obtaining the total fitness score based on all of the fitness component scores of a person.

3. The method of claim 1, wherein said muscular strength component is divided into lower extremity, upper extremity and trunk components.

4. The method of claim 3, wherein the largest share is provided to lower extremity strength at 15%, the second largest share is provided to upper extremity strength at 12%, the third largest share is provided to trunk strength at 8% for the muscular strength component in said graphical fitness map.

5. The method of claim 1, wherein the step of determining exercise strategy depending on the frequency and time of exercise for each exercise session comprises the steps of:
in each exercise session, determining rules of exercise depending on the time and frequency spared per session for each fitness component; and
designating and applying primary and secondary degrees in order to put forth the difference of scope and intensity of each component except the body composition component.

6. The method of claim 4, wherein the steps of determining are performed by software executed on a system, the software applying the following rules of:
not doing primary strength exercises in the session where primary cardio exercise is performed;
performing flexibility exercises in the sessions where primary and secondary cardio exercises are performed, applying the secondary flexibility if the time spared for flexibility exercises is up to 10 minutes; applying the primary flexibility if the time spared for flexibility exercises is more than 10 minutes;
not doing primary cardio exercises in the session where primary strength exercise is done;
not performing primary cardio, secondary cardio, primary strength and secondary strength exercises after the primary flexibility exercise.

7. The method of claim 2, wherein the step of determining the graphically represented ratios of each component with respect to the space allocated in the fitness map on the display is performed by interpolation by software executed on said system.

8. The method of claim 3, wherein the exercise strategies for components are respectively cardio strategy, strength strategy and a flexibility strategy.

9. The method of claim 1, wherein said graphical fitness map is a diagram.

10. The method of claim 1, further comprising:
re-measuring the person's following components; and
repeating the remaining steps of the method in response to changes in the person's measured fitness components.

* * * * *